(12) United States Patent
Kamen et al.

(10) Patent No.: US 9,603,622 B2
(45) Date of Patent: Mar. 28, 2017

(54) MEDICAL DEVICE INSERTION APPARATUS, SYSTEM AND METHOD

(75) Inventors: Dean Kamen, Bedford, NH (US); Brian H. Yoo, Cambridge, MA (US); Brian D. Tracey, Litchfield, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 568 days.

(21) Appl. No.: 12/910,210

(22) Filed: Oct. 22, 2010

(65) Prior Publication Data
US 2012/0101440 A1    Apr. 26, 2012

(51) Int. Cl.
*A61B 17/34*     (2006.01)
*A61M 25/06*     (2006.01)
*B23K 10/00*     (2006.01)

(52) U.S. Cl.
CPC ..... *A61B 17/3415* (2013.01); *A61M 25/0693* (2013.01); *A61B 2090/08021* (2016.02); *A61M 25/0606* (2013.01); *B23K 10/00* (2013.01)

(58) Field of Classification Search
CPC .......... A61M 25/0606; A61M 25/0693; A61M 2090/08021; A61B 17/3415
USPC ......... 604/164.08, 164.01, 168.01, 403, 404, 604/164.1, 104
See application file for complete search history.

(56) References Cited

U.S. PATENT DOCUMENTS

| | | | | |
|---|---|---|---|---|
| 4,908,021 A | * | 3/1990 | McFarlane | A61M 25/0693 604/168.01 |
| 5,000,740 A | * | 3/1991 | Ducharme | A61M 25/0631 604/162 |
| 5,312,359 A | * | 5/1994 | Wallace | 604/164.08 |
| 2005/0131350 A1 | * | 6/2005 | Shaw | A61M 25/0631 604/168.01 |
| 2006/0178635 A1 | * | 8/2006 | Callaway | 604/164.09 |
| 2007/0142786 A1 | * | 6/2007 | Lampropoulos et al. | 604/189 |
| 2009/0209912 A1 | * | 8/2009 | Keyser et al. | 604/164.1 |

* cited by examiner

*Primary Examiner* — Theodore Stigell
(74) *Attorney, Agent, or Firm* — Michelle Saquet Temple

(57) ABSTRACT

An insertion device is disclosed. The insertion device includes a base portion, a top portion slidably connected to the base portion, an introduction needle, a catheter in slidable relation to the introduction needle, and a substantially cylindrical flash chamber, the flash chamber having an inlet in fluid communication with the introduction needle. The flash chamber is connected to the base portion, the top portion slidably engages with the flash chamber, and the catheter and the top portion slidably advance with respect to the introduction needle and the base portion.

16 Claims, 45 Drawing Sheets

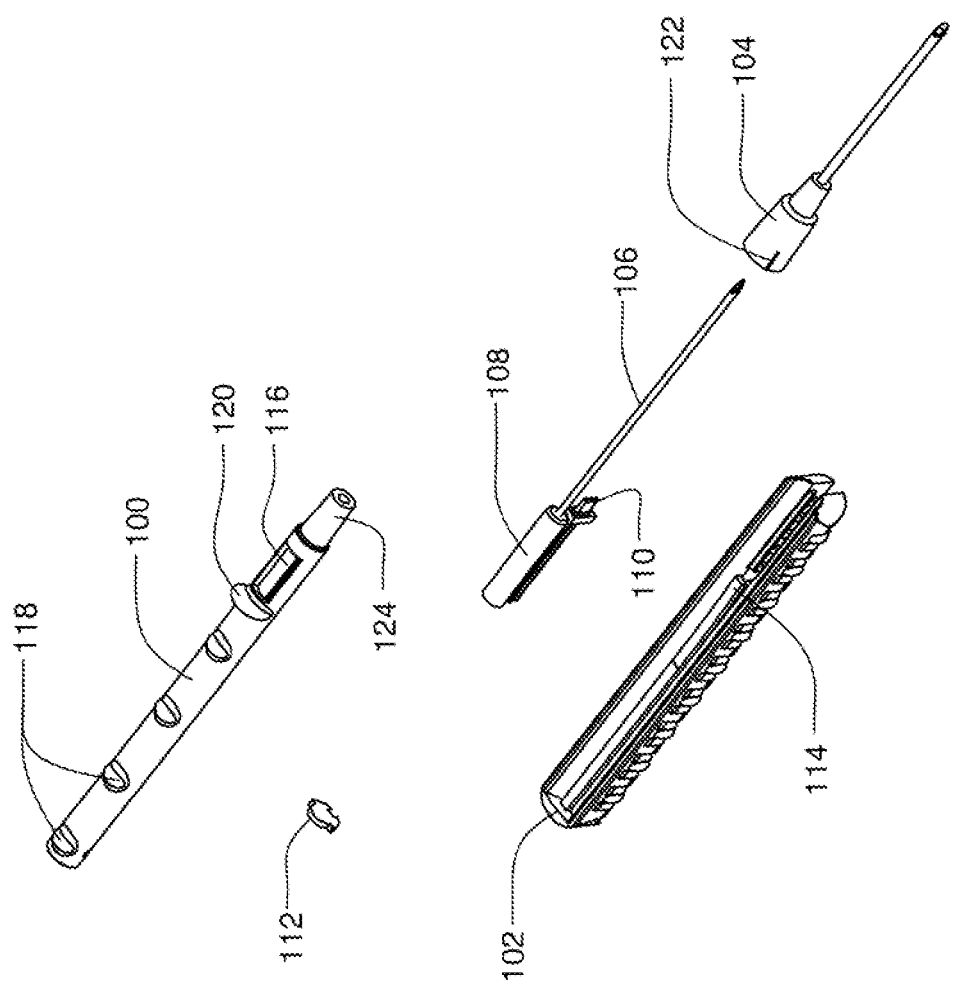

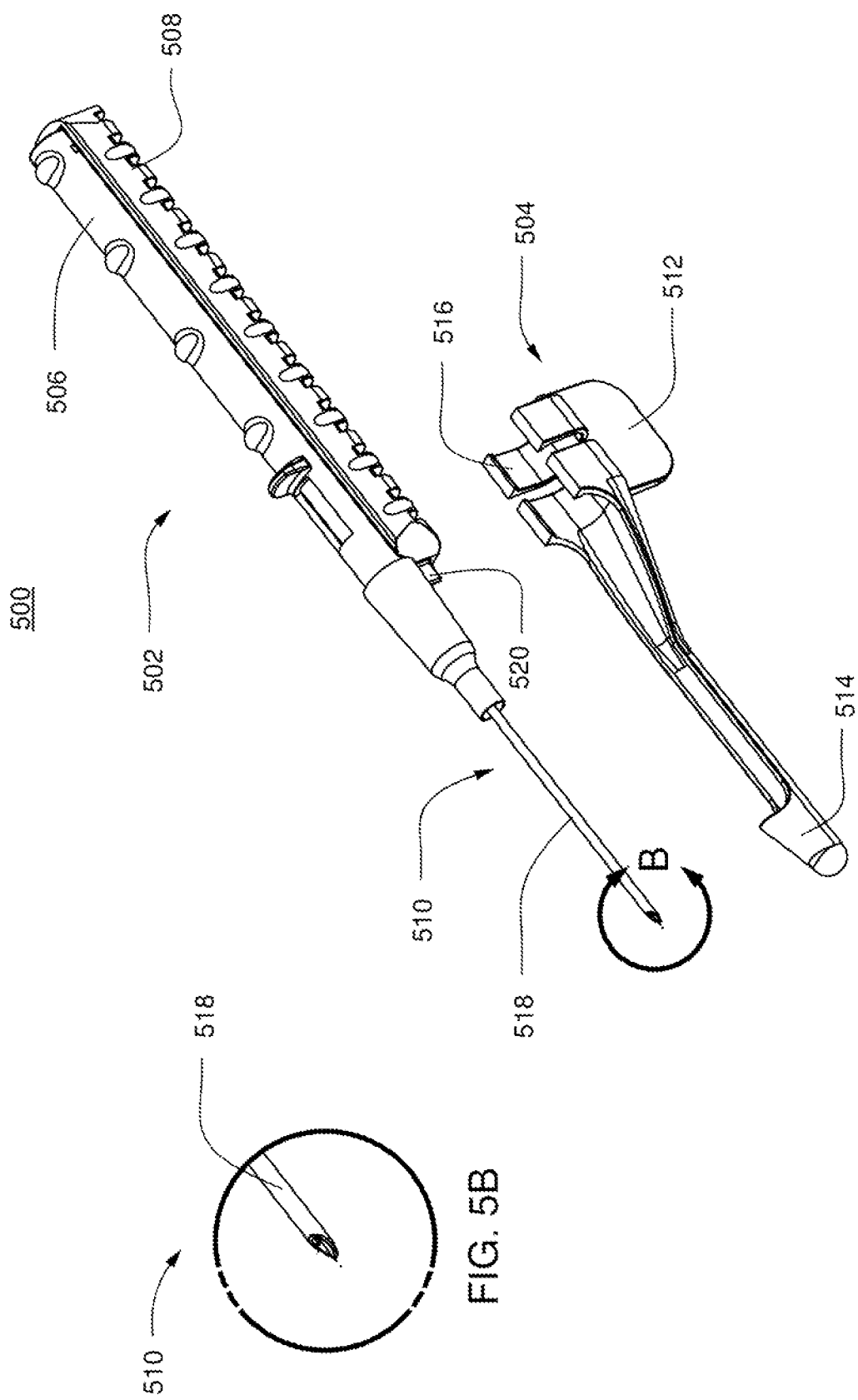

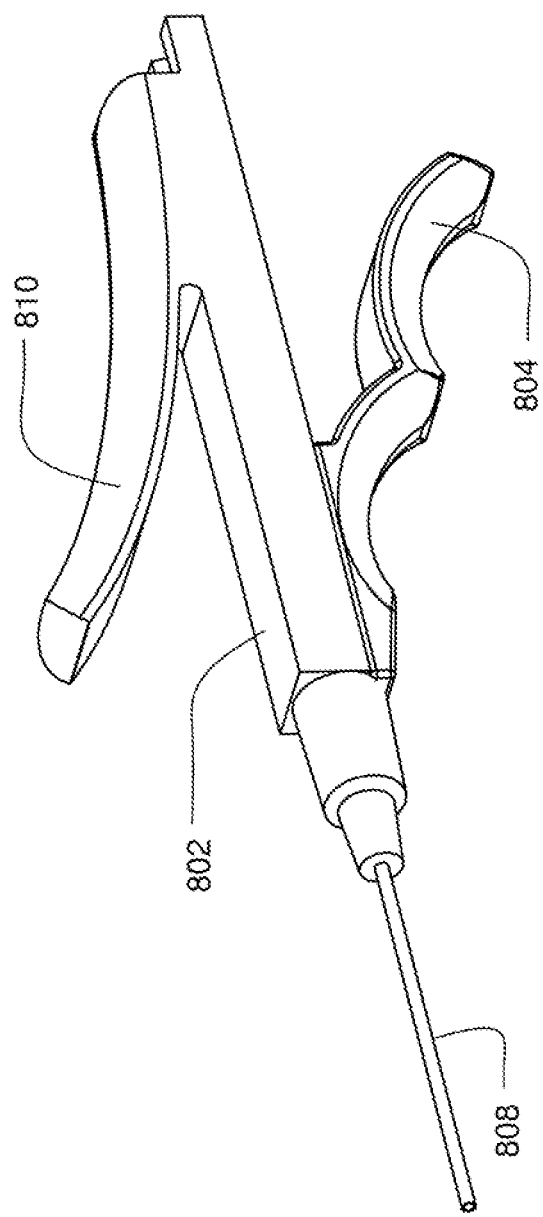

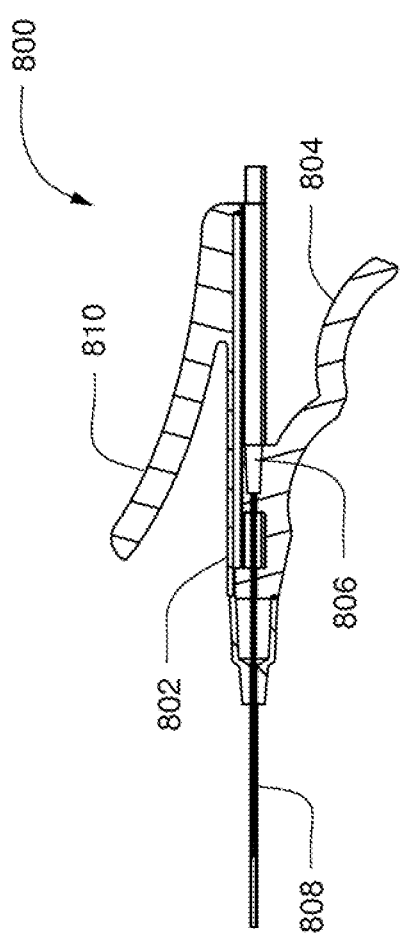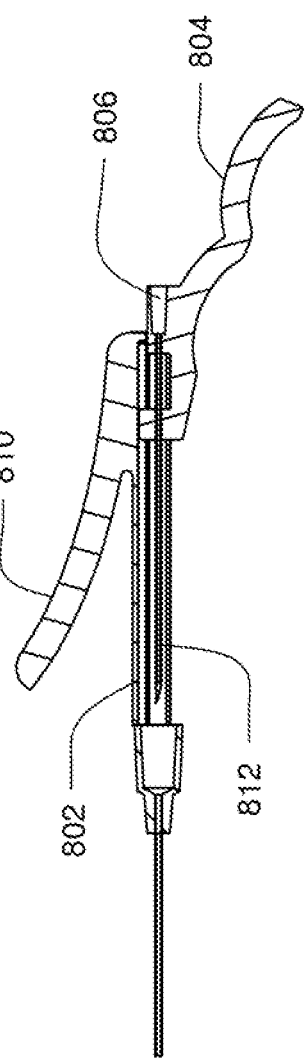
FIG. 8C
FIG. 8D

MEDICAL DEVICE INSERTION APPARATUS, SYSTEM AND METHOD

TECHNICAL FIELD

The present invention relates to medical device insertion and more particularly, to apparatus, system and method for medical device insertion.

BACKGROUND INFORMATION

Inserting a medical device into a patient may present difficulties. For example, when inserting a medical device or catheter into a patient's vein, the needle may enter the vein on one side and proceed to pierce through the opposite side, presenting an injury to the patient. Other difficulties exist with respect to releasing the catheter at the proper position such that the catheter is in the vein. Thus, difficulties exist when determining the proper time to release the catheter such that it is in the vein, but before the needle pierces the opposing wall of the vein. Additional situations regarding the insertion of a catheter or other medical device present similar difficulties, thus, the insertion difficulties are not only limited to catheters or insertion into veins.

Accordingly, there is a need for a device to aid with proper insertion of a medical device, including a catheter, into a patient that reduces the occurrence of unintentional piercing by the introduction needle and releasing the medical device or catheter prior to insertion into the desired area.

SUMMARY

In accordance with one aspect of the present invention, an insertion device is disclosed. The insertion device includes a base portion, a top portion slidably connected to the base portion, an introduction needle, a catheter in slidable relation to the introduction needle, and a substantially cylindrical flash chamber, the flash chamber having an inlet in fluid communication with the introduction needle. The flash chamber is connected to the base portion, the top portion slidably engages with the flash chamber, and the catheter and the top portion slidably advance with respect to the introduction needle and the base portion.

Some embodiments of this aspect of the present invention may include one or more of the following, in any combination or separately: wherein the flash chamber further includes an insert; wherein the insert is a cylindrical insert; and/or wherein the insert includes a color contrasting to the color of a flash fluid; and/or wherein the insert includes a material having wicking properties; and/or wherein the wicking material further includes an assay test strip wherein the assay test strip indicates the presence of one or more indicators in a fluid; and/or wherein the flash chamber further includes a filter; and/or wherein filter includes a membrane material; and/or wherein the flash chamber further includes an expandable membrane in fluid communication with the introduction needle; and/or wherein the insertion device further includes a needle guard removably connected to the base portion; and/or wherein the top portion further includes an opening to at least a portion of the flash chamber whereby the flash chamber may be viewed; and/or wherein the device further includes a locking mechanism, wherein as the top portion advances with respect to the base portion, the locking mechanism moves from an unlocked position to a locked position, whereby in the locked position, the top portion is positioned about the needle; and/or wherein the catheter further includes a distal end including a non-perpendicular angle to the axis of the catheter and an underside conforming to a keel of the introduction needle.

Additionally, some embodiments of any aspect of the present invention may include one or more of the following, in any combination or separately, wherein the device further includes a locking mechanism having a first end and a second end, the locking mechanism located on the base portion; and a clip connected to the top portion, wherein the clip adapted to accommodate and control the locking mechanism and wherein the clip slidably engages the locking mechanism, wherein as the top portion slidably advances with respect to the base portion, the clip slidably advances from the first end of the locking mechanism to the second end of the mechanism, whereby the locking mechanism moves from an unlocked to a locked position and whereby in the locked position, the top portion is positioned about the needle.

In accordance with another aspect of the present invention, an insertion device is disclosed. The insertion device includes a base portion, a top portion slidably connected to the base portion, a substantially cylindrical flash chamber, the flash chamber having an inlet and adapted for connection to an introduction needle, wherein the top portion slidably engages with the flash chamber, and a locking mechanism, wherein as the top portion advances with respect to the base portion, the locking mechanism moves from an unlocked position to a locked position.

Some embodiments of this aspect of the present invention may include one or more of the following, in any combination or separately: wherein the flash chamber further includes an insert; and/or wherein the insert is a cylindrical insert.

In accordance with another aspect of the present invention, a method is disclosed. The method includes generating 2.45 GHz Radio Frequency energy using a magnetron, moving a needle towards an object and a contact, maintaining a connection between the needle and the contact, generating a plasma arc, and moving the needle into contact with the object.

Some embodiments of this aspect of the present invention may include one or more of the following, in any combination or separately: wherein the method further includes moving the needle into contact with a die cavity for a predetermined amount of time and removing the needle from the die cavity; and/or wherein the method further includes moving the needle into contact with a plastic tube, melting the plastic tube, and cooling the plastic tube wherein the plastic tube forms a seal about the needle.

These aspects of the invention are not meant to be exclusive and other features, aspects, and advantages of the present invention will be readily apparent to those of ordinary skill in the art when read in conjunction with the appended claims and accompanying drawings.

BRIEF DESCRIPTION OF THE DRAWINGS

These and other features and advantages of the present invention will be better understood by reading the following detailed description, taken together with the drawings wherein:

FIG. 5A is a partial exploded view of the system in the unlocked position according to one embodiment;

FIG. 5B is a magnified view of the indicated section in FIG. 5A;

FIGS. 8A-8B are views of one embodiment of the device;

FIGS. 8C and 8D are views of one embodiment of the device;

DETAILED DESCRIPTION

The device and methods include an insertion device. The device may be used to insert an object, e.g., a medical device, into a patient, whether human or otherwise. In the exemplary embodiment, the device may be used to insert a catheter into a vein, for example, inserting an IV catheter. However, the device may be used for other applications, including, but not limited to, other vascular access application. The device may be beneficial for many reasons, including, but not limited to, increasing the success rate of insertion of the medical device and decreasing and/or limiting the trauma to the vessel during insertion.

In some embodiments of the device, the device includes an introduction needle and a catheter. The introduction needle may be located inside the catheter before the catheter is inserted into a patient. The introduction needle may be connected to the device, and the catheter may be inserted over the introduction needle. In some embodiments, the introduction needle and catheter are manufactured and packaged in an assembled fashion.

The device may be used to insert a catheter into a patient such that the introduction needle includes an opening that would enter the vein concurrent with or subsequent to the catheter entering the vein. The opening may be in fluid connection with a "flash chamber" in the device which allows for blood, or flash fluid, from the vein, or otherwise fluid from the area of the desired catheter destination, to flow through the hole in the introduction needle to the flash chamber. Thus, blood, or flash fluid, entering the flash chamber may indicate that the catheter has entered the vein/desired location. In various embodiments, the flash chamber may be located on the device such that a user may view the flash chamber easily while inserting the catheter.

Although discussion regarding the use of the insertion device for inserting a catheter into a vein is used throughout this description as an exemplary embodiment, the device is not limited to use as a catheter inserter into a vein and may be used to insert a catheter into other places on a patient's body. In some embodiments, the fluid visible in the flash chamber may be blood, and in other embodiments, the fluid visible in the flash chamber may be another bodily fluid, which may include, but is not limited to, urine and spinal fluid. In addition to catheters, in some embodiments, the device described may be used for insertion of various medical devices, including, but not limited to, needles, RFID chips, vascular access application and analyte sensors.

Various methods of making the introduction needles, various shapes of the catheter as well as various embodiments of the device are described herein. However, these are not meant to be limiting, rather, they are illustrative examples of various embodiments.

Figure 1A:
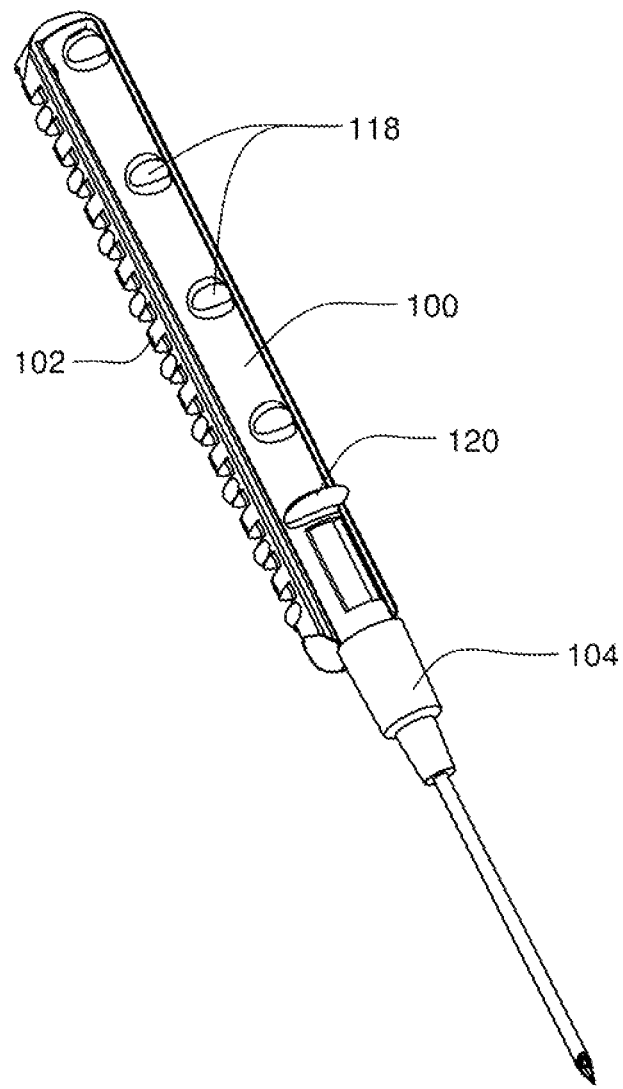
FIG. 1A is a view of a device according to one embodiment.
Figure 1C:
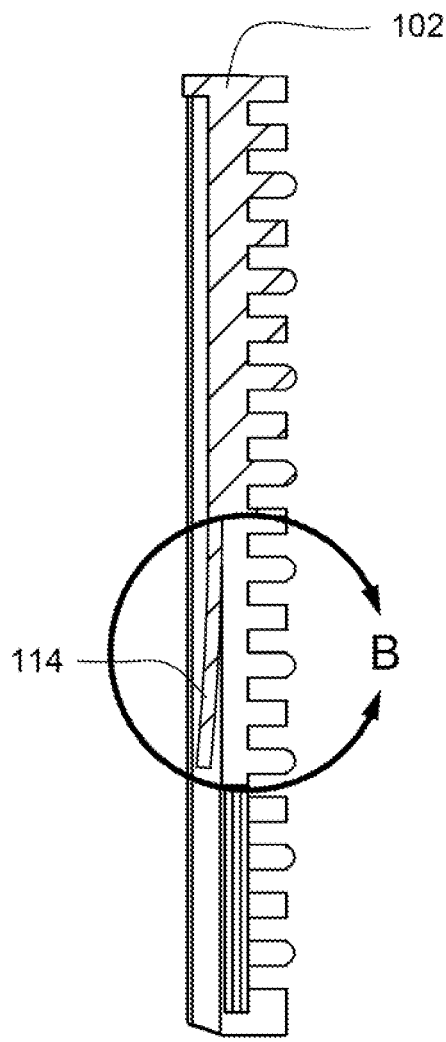
FIG. 1B is an exploded view of the device shown in FIG. 1A.
FIG. 1D is a magnified view of section "B" in FIG. 1C.
FIG. 1E is view of a clip according to one embodiment.
FIGS. 1F-1G are views of the locking mechanism in the locked and unlocked position; according to one embodiment.
FIG. 1H is a bottom view of a top portion of a device according to one embodiment.
Figure 1D:
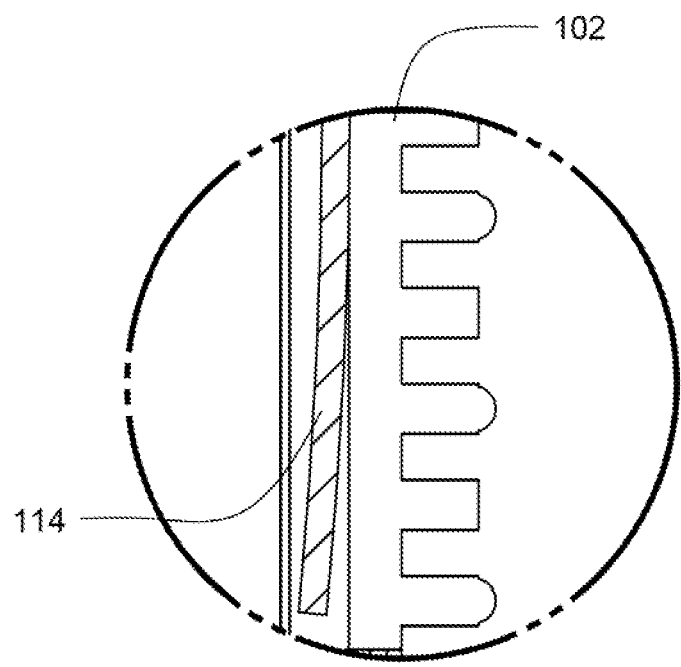
Figure 1E:
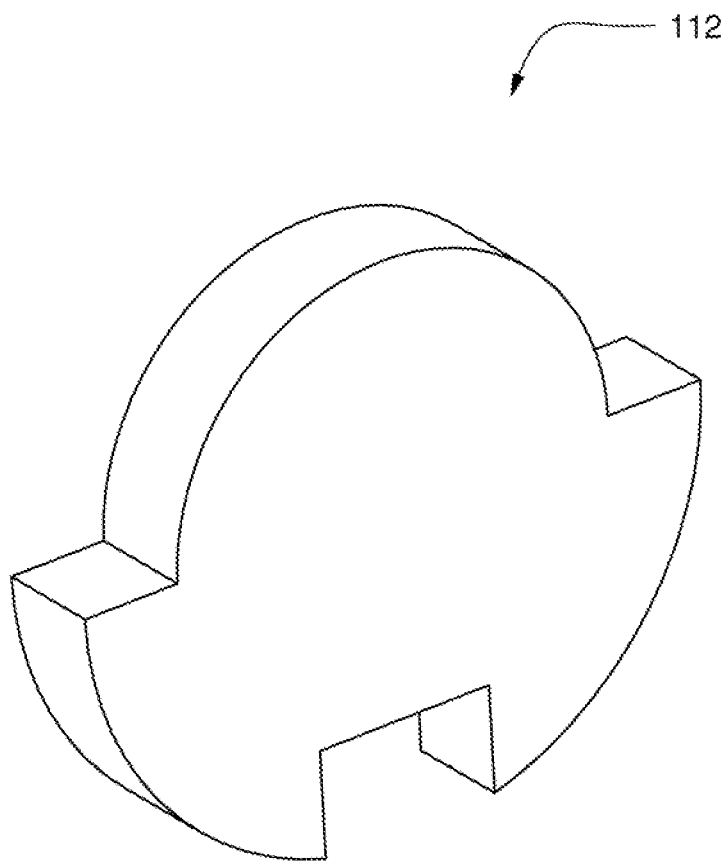
Figure 1F:
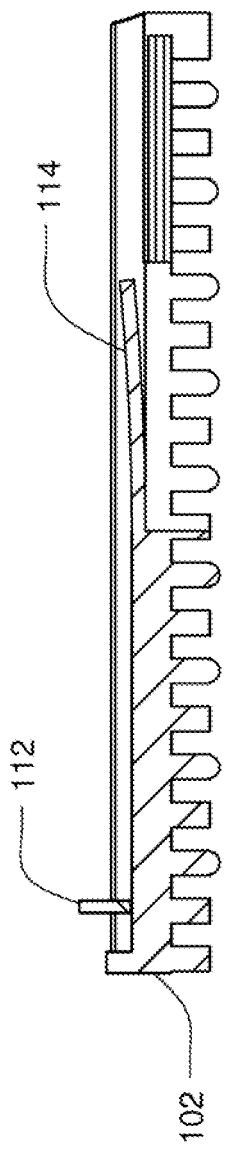
Figure 1G:
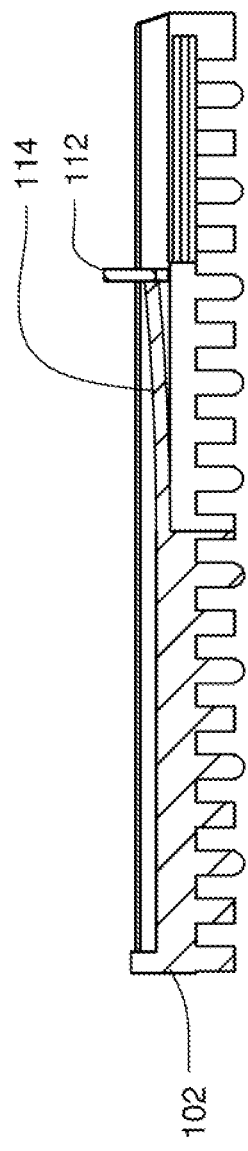

Referring first to FIGS. 1A-1B, an exemplary embodiment of an insertion device is shown. Various embodiments of the insertion device are described herein and additional embodiments may include one or more features from one or more of the various embodiments in combination, forming additional embodiments. Thus, the various embodiments and combinations shown and described herein are not meant to be limiting, rather, examples of the multitude of embodiments.

In various embodiments of the device, the device may include a top portion 100 and a base portion 102. The top portion 100 and base portion 102 may be slidably connected. In some embodiments, the top portion 100 may slide over a portion of a flash member 108. In some embodiments, a relief-and-protrusion type mechanism relationship may provide the sliding mechanism for the top portion 100 with respect to the base portion 102.

Figure 1H:
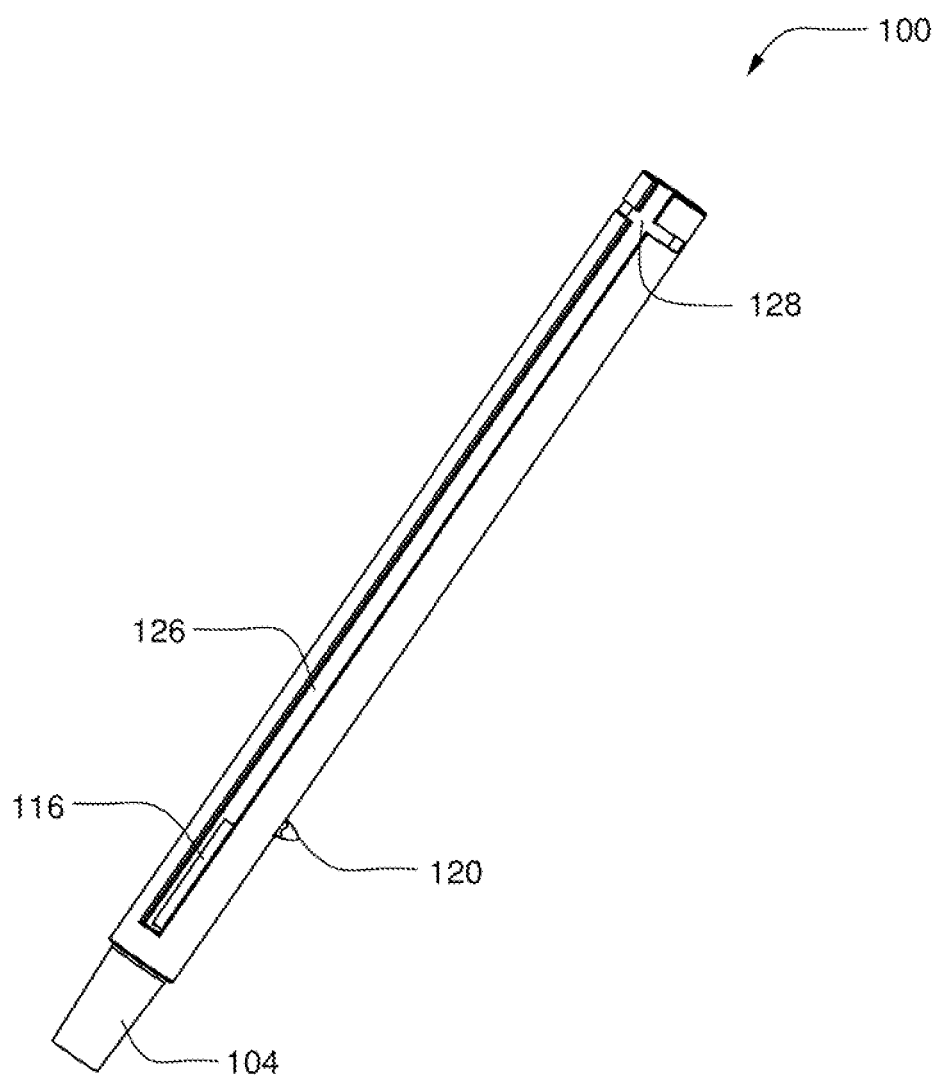

In some embodiments, the flash member 108 may be attached to the base portion 102 and the top portion 100 may include a feature to accommodate the shape of the flash member 108 such that the top portion 100 may slide over the flash member 108, may be which may be connected to the base portion 102. Referring now also to FIG. 1H, in the exemplary embodiment, the top portion 100 is a substantially hollow cylindrical portion and may include an open area 126 to accommodate the flash member 108. Additionally, in the exemplary embodiment, the top portion 100 may include a window 116, which, in the exemplary embodiment, is an opening in the top portion 100 such that the flash member 108 may be visible when positioned above the flash member 108. Although not shown in the exemplary embodiment, in some embodiments, the flash member 108 may be connected or attached to the top portion 100 and another embodiment of the sliding mechanism may be used for the top portion 100 to slidably advance with respect to the base portion 102.

The top portion 100 and base portion 102 may be made from a transparent plastic material, including, but not limited to, one or more of the following: polyester, acrylic and polycarbonate and for any thermoplastic. However, in some embodiments, the top portion 100 and/or base portion 102 may be made from non-transparent materials, including, but not limited to, FEP/TPEP (TEFLON). In the exemplary embodiment, the top portion 100 may be made transparent and the base portion 102 non-transparent material. As discussed in greater detail below, the flash member 108 may be made transparent while the insert non-transparent, or, white, in the exemplary embodiment.

Although the exemplary embodiment and various other embodiments of the device are described herein, the shapes and sizes of the various parts of the various embodiments are not limited to those described herein. Thus, the shapes and sizes may vary in various embodiments.

Figure 2A:
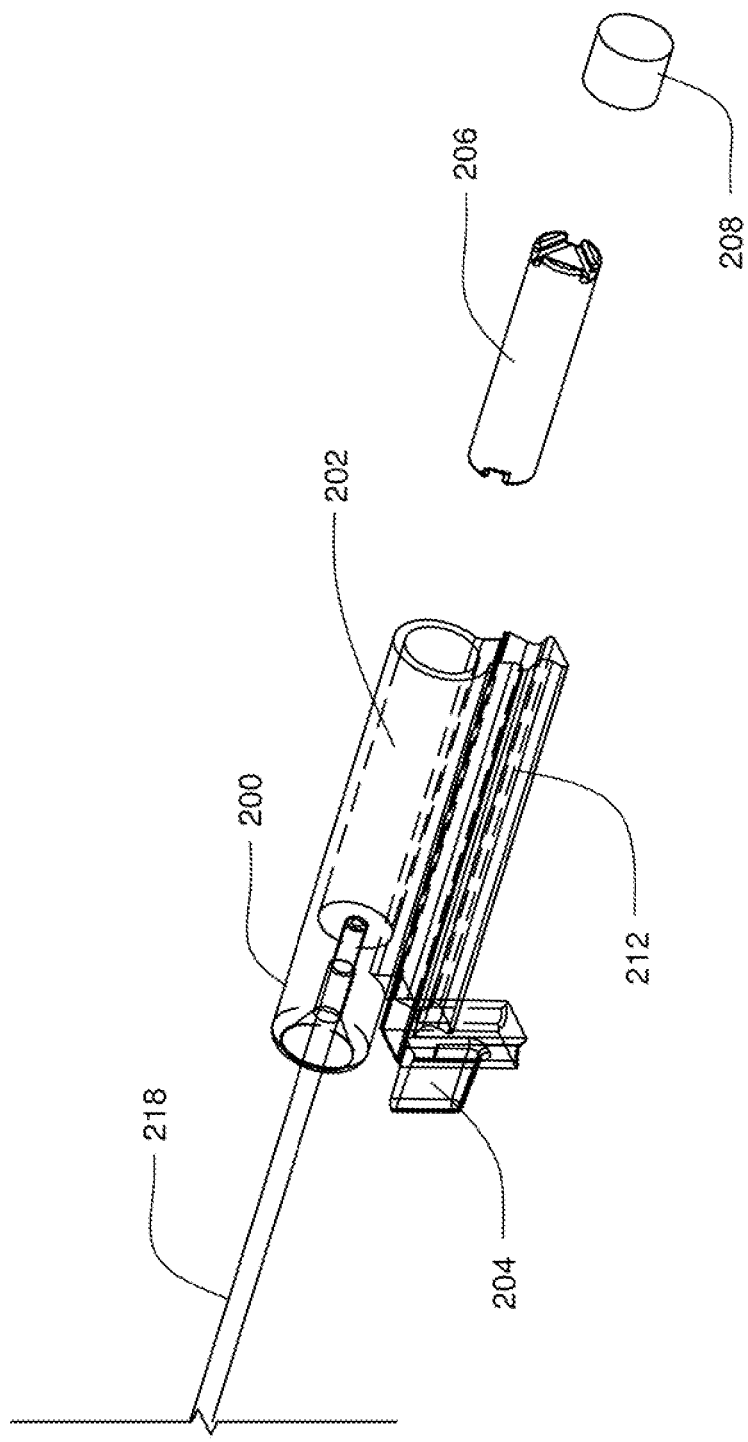
FIGS. 2A-2C are various partial views of the device according to one embodiment.
Figure 2B:
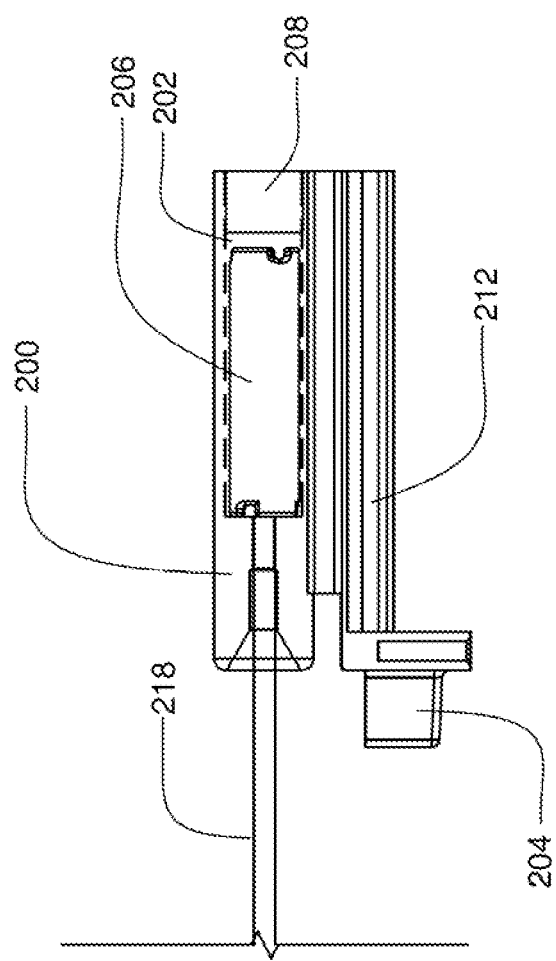
Figure 2C:
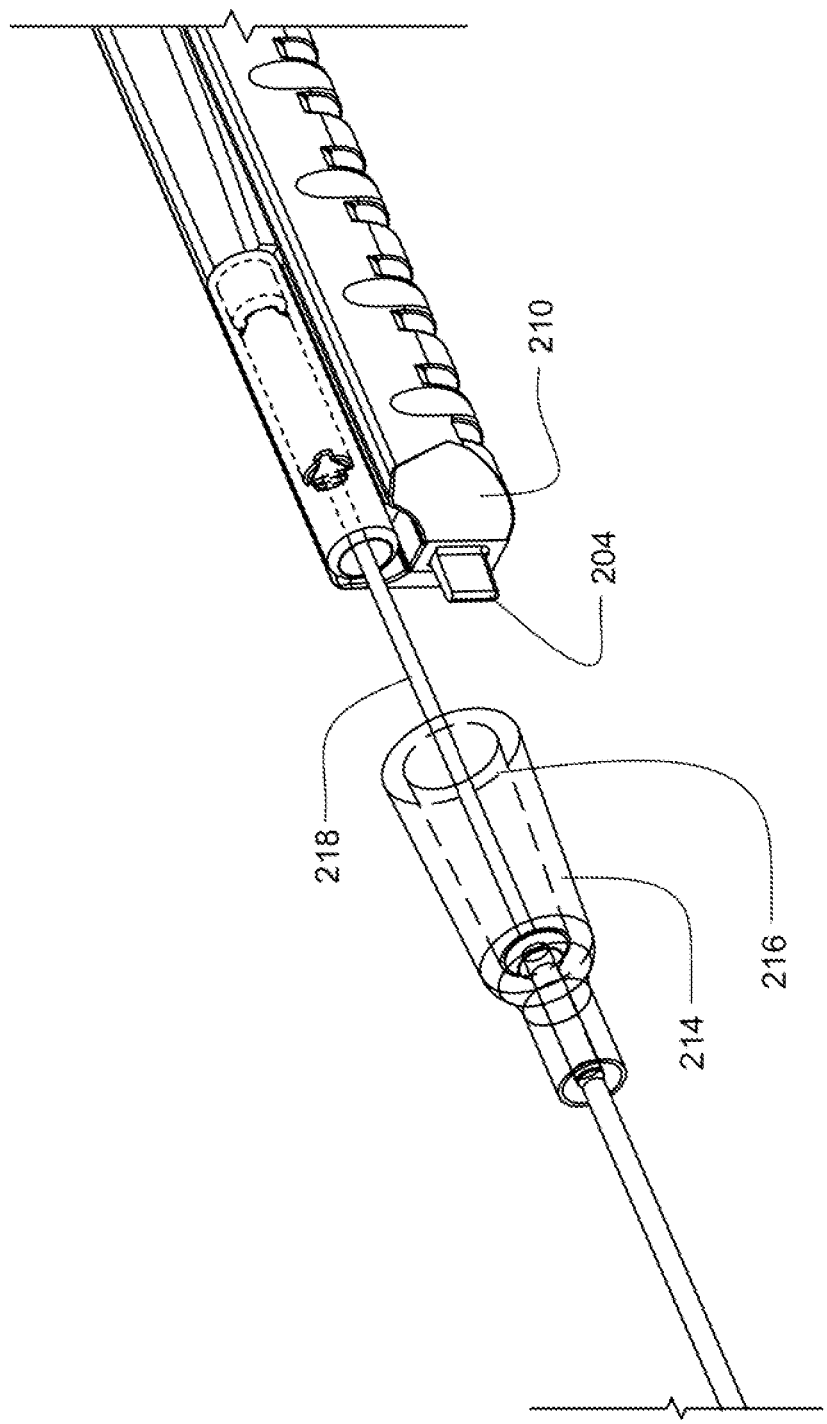

Referring now to FIGS. 2A-2C, the flash member 200 is shown with the flash chamber 202. The flash member 200 includes a connection section 212 for connecting to the base member 210, in the exemplary embodiment, and a position tab 204 for maintaining the clock of the catheter assembly 214 or medical device assembly to be inserted onto the top portion (not shown, shown in FIGS. 1A-1B as 100). The flash member 200 includes a flash chamber 202. In various embodiments, the introduction needle 218 is in fluid communication with the flash chamber 202. In some embodiments, the bore of the introduction needle 218 is in fluid communication with the flash chamber 202. Thus, the hole/opening in the introduction needle 218 provides the path for the flash fluid to flow to the flash chamber 202.

In some embodiments, the flash chamber 202 may be cylindrical. In some embodiments, the flash chamber 202 may be hollow. Some embodiments of the flash chamber 202 include wherein the inside wall of the hollow flash chamber 108 may include, but are not limited to, one or more of the following features: textured, raised, grooved and/or rib-like features. Some embodiments may include a flash chamber 202 that is shaped other than cylindrical, including, but not limited to, a hollow rectangular shape or a hollow square shape.

In some embodiments, the flash chamber 202 may include an insert 206. As shown in the exemplary embodiment, the insert 206 may be cylindrical. In some embodiments, the insert 206 may be hollow, however, in some embodiments; the insert 206 may be solid. In the exemplary embodiment, the insert is constructed of a color or a texture to provide contrasts to the fluid, e.g., blood, that enters the flash chamber 202. For example, in the exemplary embodiment, where the fluid is blood, the insert 206 may be white to provide contrast to the red blood. However, in some embodiments, the insert 206 may be any coloration or texture, including, but not limited to, one or more of the following features: raised, grooved and/or rib-like features, that provides sufficient contrast such that the presence of the fluid may be easily ascertainable by a user. This may be greatly advantageous as, in many instances, while inserting a catheter, for example, into a patient, it may be difficult to differentiate between the flash fluid and, for example, the patient's skin/fur/hair tone or the patient's clothing. Thus, by enabling the user to readily discern the flash fluid, the user will readily cease to further insert the needle and insert the catheter, preventing piercing of the opposite side of the vein.

The insert 206 displaces a portion of the total volume of the flash chamber 202. In the exemplary embodiment, the insert 206 displaces a portion of the center flash chamber 202, thus, the flash fluid may be visible through 360 degrees of the cylindrical flash chamber 202. Thus, in the exemplary embodiment, the cylindrical insert 206 provides for 360 degree flash viewing in the flash chamber 202, however, the insert 206, displacing a portion of the volume of chamber, a smaller volume of flash fluid is necessary to fill the flash chamber 202, and hence, the flash fluid may be readily discerned at a faster rate. In the exemplary embodiment, the flash fluid forms a thin layer about the flash cylindrical insert 206, which may be sufficient, as the cylindrical insert 206 may be a contrasting color, e.g. white, compared with the flash fluid, e.g. blood.

Still referring to FIGS. 2A-2C, in the exemplary embodiment, the flash member 200 includes a filter 208 at the end of the flash chamber 202. The filter may be a porous filter that allows air to pass and does not allow the flash fluid to pass through the filter. In various embodiments, the porous filter may be made from one or more, but not limited to, the following: PTFE or HDPE. In some embodiments, the porous filter may be replaced with a membrane material, for example, one made from PCTW or polyester. In these embodiments, the membrane may be welded to the end of the flash chamber 202.

In the exemplary embodiment, the flash chamber 202 is a capillary action flash chamber 202. However, in various other embodiments, the flash chamber 202 may be a wicking action flash chamber 202. In these embodiments, the flash chamber 202 may include an insert of wicking material, or, a material having wicking properties, which may include, but is not limited to, cotton, cotton blends, hydrogels or a porous polyethylene, or PTFE material, which may include, but is not limited to, POREX, made by POREX Technologies, Fairburn, Ga., or another porous polymer. In some embodiments, the wicking material insert may be coated with one or more coatings to ensure wicking but not dripping. In some embodiments including a flash chamber 202 applying a wicking action, a vent may be used, rather than filter or membrane.

In some embodiments, the wicking material may also include an assay test strip or an assay embedded into the wicking material that, upon contact with the flash fluid, may indicate the presence of one or more, but not limited to, the following: proteins, compounds (including, but not limited to, pharmaceuticals, nutrients, controlled substances, etc), viruses, parasites, and/or elements, diseases or conditions. For example, the assay may indicate the presence of human chorionic gonadotropin (hCG), indicating pregnancy, and/or the presence of a virus, or parasite, for example, through a reaction of the fluid to an antibody in the wicking material. In some embodiments, by detecting the presence of proteins, compounds, viruses, and/or parasites, this may prevent a medical error that may cause harm to the patient, for example, administering a medication that may be harmful to a pregnant woman, and/or react with the presence of another drug already in the blood stream, etc.

In some embodiments, the flash chamber 202 may include a membrane or bag fluidly connected to the introduction needle. In some embodiments, the membrane or bag may be made from one or more of, but not limited to, the following: polyethylene, polyurethane, or other thin-film plastics or elastomers. Thus, in these embodiments, the bag may fill with flash fluid as the introduction needle enters the area for medical device insertion, e.g., the vein. In these embodiments, a vent, and/or a layer of material the same or similar to the flash chamber 202 material having at least one opening, may be used replacing the filter or membranes discussed above, to seal the flash chamber 202. In other embodiments of this embodiment, the flash chamber 202 may not include a vent or filter.

Still referring to FIGS. 2A-2C, the flash member 200 may, in some embodiment, include an position tab 204 for maintaining the position or clock of the catheter assembly 214. In some embodiments, the catheter assembly 214 may include a groove 216 or other like feature wherein the position tab 204 fits in a tongue-and-groove arrangement. Thus, the catheter assembly 214 clock position is maintained by the position tab 204 preventing the twisting of the catheter assembly 214 with respect to the device to maintain correct placement for insertion. As discussed in more detail below, in some embodiments, it is desirable to maintain the space over the opening in the introduction needle such that the flash fluid may flow to the flash chamber 202. As such, were the catheter assembly 214 to move to another position, the opening in the introduction needle may be occluded and as such, the flash fluid may not flow to the flash chamber 202 as quickly as it might. Thus, the position tab 214 maintains the device such that optimal usage of the device may be employed. Although a groove 216 is shown, in some embodiments, where, for example, the catheter assembly 214 includes a threaded portion, the groove may be created by a space formed by the raised threaded portion. In other embodiments, various features may be introduced to the catheter assembly 214 to interact with the position tab 204 and maintain the position of the catheter assembly 214. Various other embodiments may include a different mechanism than those presented herein for maintaining the clock of the catheter with respect to the device.

The flash member 200, in the exemplary embodiment, is made from plastic, which materials may include, but are not limited to, one or more of the following, alone or in combination: polyester, acrylic and polycarbonate and/or any thermoplastic. In the exemplary embodiments, the flash member 200 is made from transparent material. As shown in FIG. 2C, the flash member 200 may be adhered to the base member 210 by way of the connection section 212. In other embodiments, where the flash member 200 is not transparent, the flash member 200 may be made from FEP/TPEP (TEFLON), or any of the other materials discussed above.

An introduction needle 210 may be attached to the flash chamber 202 and may provide a fluid connection between the introduction needle 210 and the inside of the flash chamber 202. In some embodiments, the introduction needle may be made from 304 or 306 stainless steel, however, in other embodiments; the introduction needle may be made from any material desired including, but not limited to, a different grade stainless steel, polycarbonate or plastic. In the exemplary embodiment, the introduction needle is 2 inches long and may be a 20 gauge needle. However, in other embodiments, the length of the introduction needle 210 and the gauge may be greater or less than the values described herein and may depend on one or more of but not limited to, the following: the medical device, the location of insertion and the patient.

Referring now to FIGS. 1A-1H, in some embodiments, the top portion 100 and/or the base portion 102, may include raised, ribbed or otherwise textured features 118 to assist, for example, in maintaining a steady grip on the device. Additionally, in some embodiments, the top portion 100 may include a thumb feature 120 which may assist in pushing the top portion 100 forward with respect to the base portion 102 so as to advance the top portion 100. In the exemplary embodiment, the features 118 may be as shown which may be desirable to accommodate different style/methods of gripping by the user and/or left handed or right-handed users.

A catheter assembly 104 may be removably attached to the end 124 of the top portion 100 of the device. As discussed above, in some embodiments, a mechanism for maintaining the clock or position of the catheter with respect to the device is used. In some embodiments, this mechanism may include a tongue and groove mechanism, i.e., a position tab 110 on the flash member 108 and a groove 122 on the catheter assembly 104. In the exemplary embodiment, the catheter assembly 104 is simply placed onto the end 124 of the top portion 100, without further connection, and the clock of the catheter assembly 104 maintained by the position tab 110 together with the groove 122. However, in other embodiments, the catheter assembly 104 may be removably attached to the top portion 100, and in some embodiment, the catheter assembly 104 may removably snap fit or otherwise connect to the top portion 100, however, in these embodiments, the user is able to release the catheter assembly 104 when desired.

The bottom of the top portion 100 is shown (see FIG. 1H). In the exemplary embodiment, the top portion 100 includes an open area 126 to accommodate the flash member 108 such that the top portion 100 slidably engages with the flash member 108. As discussed above, other mechanisms may be used to establish a sliding relationship between the top portion 100 and the base portion 102 and thus, the bottom of the top portion 100 may vary accordingly in other embodiments to accommodate the various sliding mechanisms. In the exemplary embodiment, the top portion 100 slides forward with respect to the base portion 102, and the open area 126 slides along the flash member 108, until the end of the top portion 100 is positioned at the back of the flash member 108. In the exemplary embodiment, the travel distance is sufficient such that the top portion 100 essentially reaches the end of the introduction needle 106. However, the distance traveled may vary in various embodiments. In some embodiments, the distance traveled by the top portion 100 may be dependent on at least, but not limited to, one or more of the following: length of the introduction needle 106, size of the flash member 108, length of the top portion 100.

In the exemplary embodiment, the device includes a locking mechanism whereby the top portion 100, having traveled the full distance with respect to the base portion 102, will release a locking mechanism to maintain the device in a locked position, such that the top portion 100 is locked into the fully traveled distance with respect to the base portion 102. In this position, in the exemplary embodiment, the top portion 100 is locked in a position and the introduction needle 106 is essentially inside the hollow cylindrical top portion 100. This may be desirable to essentially provide a "sharps container" for the introduction needle 106 such that the introduction needle 106 is protected by the top portion 100 when the device is in the locked position.

In the exemplary embodiment, the locking mechanism 114 includes an unlocked position, whereby the top portion 100 may slide, and in the exemplary embodiment, the top portion 100 may slide along the flash member 108, until reaching the full travel distance, which, in the exemplary embodiment, is at the far end of the flash member 108. The locking mechanism also includes a locked position, whereby the top portion 100 may no longer slide with respect to the base portion 102, and is locked in place.

Still referring to FIGS. 1A-1H, and more specifically to FIGS. 1C-1H, in the exemplary embodiment, the locking mechanism 114 includes a first end, towards the far end of the base portion 102, and a second end, towards the near end of the base portion 102, wherein the near end is the end closest to the introduction needle 106 in the exemplary embodiment. In the exemplary embodiment, a clip 112, which is located in a groove 128 in the top portion 100, accommodates the locking mechanism 114, such that the clip 112 slides along the locking mechanism 114 as the top portion 100 advances with respect to the base portion 102. The clip 112 controls the locking mechanism 114 in that the clip 112 maintains the locking mechanism 114 in an unlocked position while the top portion 100 is advancing by sliding onward with respect to the base portion 102. At the point where the top portion 100 has reached the full distance of travel, the clip 112 is at a position no longer interacting with the locking mechanism 114 and at this position; the locking mechanism 114 is in a locked position. In the exemplary embodiment, once the locking mechanism 114 is in the locked position, the top portion 100 is locked in the full distance position and thus, in the exemplary embodiment, is locked over the introduction needle 106.

Although an exemplary embodiment of the locking mechanism is described herein, other embodiments may be implemented to accomplish a similar result, namely, locking the top portion 100 with respect to the base portion 102 once the top portion 100 reaches a predetermined location with respect to the base portion 102. Although in the exemplary embodiment, the predetermined location is when the far side of the top portion 100 reaches the far side of the flash member 108, in other embodiment, the full distance or predetermined location may vary and the design of the locking mechanism may vary accordingly.

In the exemplary embodiment, the device may be used to insert a catheter into a vein of a patient. Referring now to FIG. 3A, a cross section of the distal end (with respect to an insertion device) of a standard catheter is shown. The standard catheter is a plastic tube structure and provides a symmetrical cross-section.

Figure 3B:
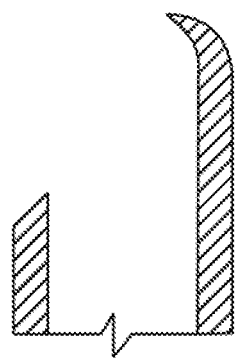
FIG. 3B is a partial cross-sectional view of a catheter according to one embodiment.
Figure 3A:
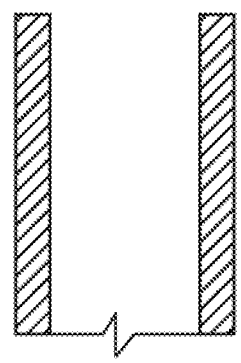
FIG. 3A is a partial cross-sectional view of a standard catheter.

Referring now to FIG. 3B, a cross section of the distal end (with respect to an insertion device) of a catheter according to the exemplary embodiment is shown. The distal end of the exemplary embodiment of the catheter includes an angled cut, other than perpendicular to the axis of the catheter, thus, the cut is non-perpendicular angle to the axis of the catheter. Additionally, a section of the distal end of the catheter includes a shape conforming to a keel of the introduction needle 106 (shown in FIG. 4B as 402).

Figure 4A:
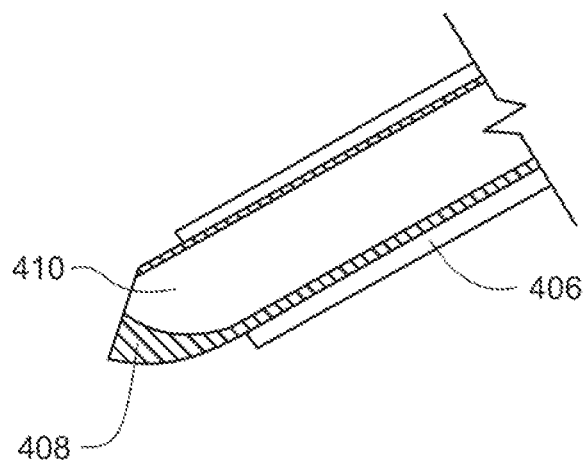
FIG. 4A is a partial cross-section view of a standard catheter and introduction needle according to one embodiment.
Figure 4B:
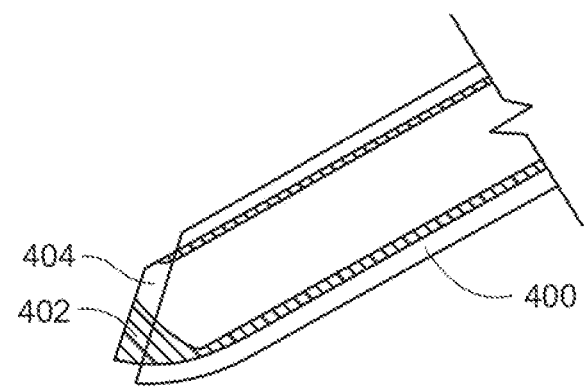
FIG. 4B is a partial cross-section view of a catheter and introduction needle according to one embodiment.

Referring now to FIGS. 4A and 4B, cross sectional drawings of two embodiments of a catheter and introduction needle assembly are shown. Referring first to FIG. 4A, a catheter similar to the catheter shown in FIG. 3A is shown together with an introduction needle 408. The needle opening 410 is shown at the front side distal end of the needle. In practice, an assembly such as this may function to provide flash fluid as the front side distal end opening 410 of the needle 408 enters the vein, the flash fluid may be visible in a flash chamber before the catheter 406 enters the vein. Thus, a user, upon seeing the flash fluid, may assume the catheter 406 has entered the vein, when in fact, it is possible the catheter 406 has not entered the vein. As such, the user may remove the needle 408 from the vein and find the catheter 406 is not in the vein. In other instances, as the user may attempt to avoid the unsuccessful insertion as described above, the user may overcompensate and insert the needle 408 deeper into the vein, risking piercing the opposite side of the vein.

Referring now to FIG. 4B, an exemplary embodiment of the catheter 400 and introduction needle 402 assembly is shown. In this embodiment, the catheter 400 is similar to the catheter shown in FIG. 3B. The needle 402 has a keel portion underside section at the distal end of the needle 402. The keel portion may be beneficial to improve the ease of insertion, e.g., into a vein, and may reduce the risk of unintentional opposite wall piercing. The needle opening 404 is located on the top side of the needle and the distal end of the catheter 400 is located on the horizontal axis with the needle opening 404. Additionally, the catheter 400 is shaped such that it conforms to the keel portion of the underside distal portion of the needle 402. The angular cut being non-perpendicular to the axis of the catheter has many advantages including, but not limited to the following wherein the exemplary embodiment cut: provides that the catheter 400 to conform to the keel portion of the needle 402; provides the needle opening 404 to be unobstructed by the catheter 400; and provides a higher incidence of successful insertion whereas when the flash fluid flows to the flash chamber, the catheter 400, being horizontally aligned with the needle opening 404, is at least partially inserted, e.g., has entered the vein. Thus, the exemplary embodiment, shown in FIG. 4B, of the catheter 400 and introduction needle 402 assembly may provide for greater rates of insertion success.

As discussed above, and referring also to FIGS. 2A-2C, the flash member 200 may, in some embodiment, include a position tab 204 for maintaining the position or clock of the catheter assembly 214. In some embodiments, the catheter assembly 214 may include a groove 216 or other like feature wherein the position tab 204 fits in a tongue-and-groove arrangement. Thus, the catheter assembly 214 clock position is maintained by the position tab 204 preventing the twisting of the catheter assembly 214 with respect to the device to maintain correct placement for insertion. With respect to the embodiment of the catheter and introduction needle assembly shown in FIG. 4B and described above, it is desirable to maintain the needle opening 404 such that the flash fluid may flow to the flash chamber 202. As such, were the catheter assembly 214 (or 400 in FIG. 4B) to rotate to another position, the opening 404 in the introduction needle 402 may be occluded and as such, the flash fluid may not flow to the flash chamber 202 as quickly as it might. Thus, the position tab 214 maintains the device such that optimal usage of the device may be employed. As discussed above, various embodiments may include a different mechanism than those presented herein for maintaining the clock of the catheter with respect to the device.

In the exemplary embodiment, the catheter may be an 18 gauge catheter, however, in various other embodiments, the gauge of the catheter may be a greater or lower gauge. In the exemplary embodiment, the catheter may be 1.16 inches long, however, in other embodiments; the catheter may be longer or shorter.

Figure 5C:
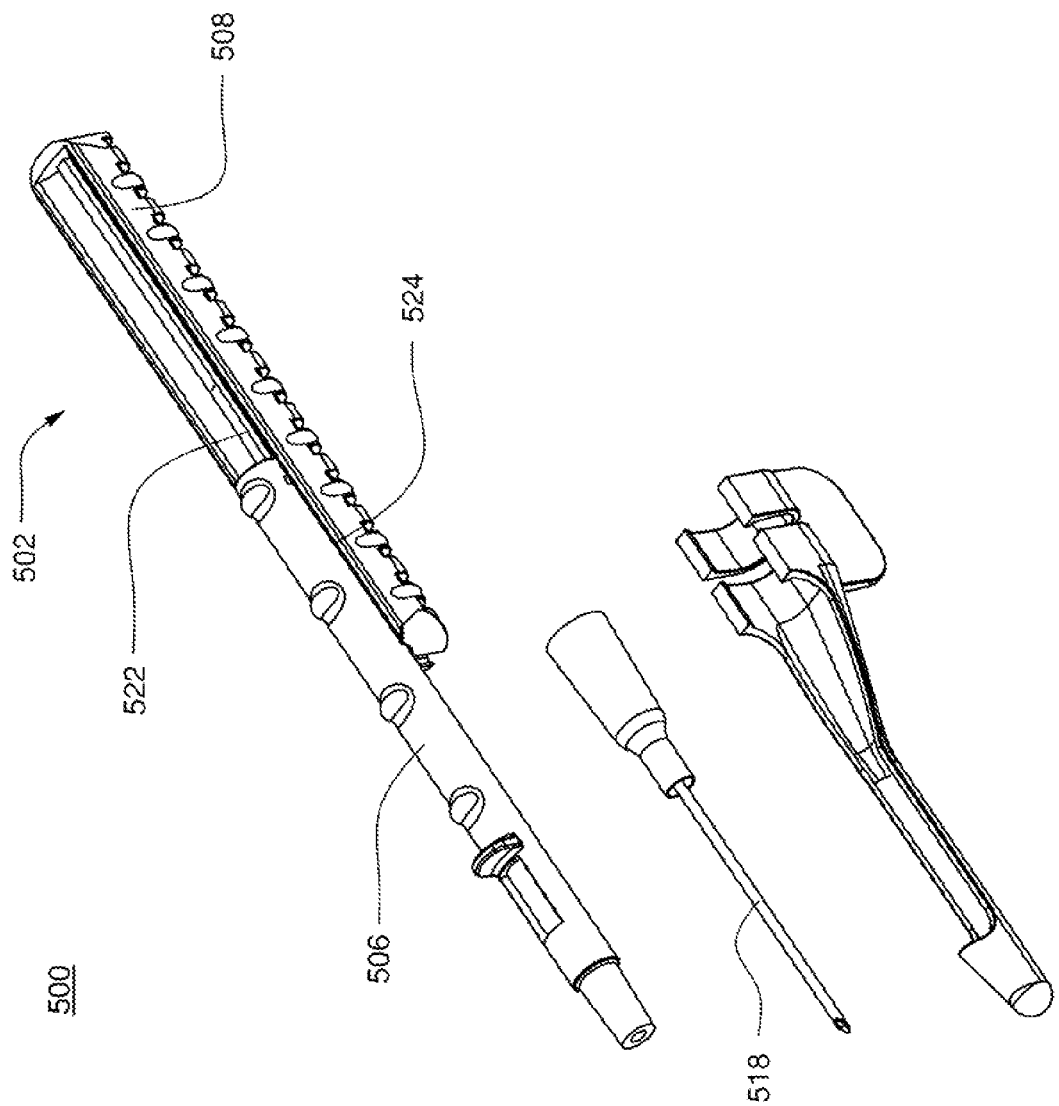
FIG. 5C is a partial exploded view of the system in the locked position according to one embodiment.

Referring now to FIGS. 5A-5C, a system for inserting a medical device is shown. In this embodiment, the system includes the exemplary embodiment of the insertion device 502, described above, as well as a protective sheath 504. As shown in FIG. 5A, the device 502 is in an unlocked and starting position. The top portion 506 and base portion 508 are aligned one to another and the catheter assembly 510 (including both the introduction needle and the catheter) is connected to the device, the catheter removably connected to the top portion 506 and the introduction needle connected to the flash member (not shown). The protective sheath 504 is shown unattached to the device 502, however, in the exemplary embodiment, the device 502, prior to use, may include the protective sheath 504 attached to the device 502. In the exemplary embodiment, the protective sheath 504 includes a pull tab 512, a catheter assembly guard 514, and a connective portion 516, connected to both the pull tab 512 and the catheter assembly guard 514. The catheter assembly guard 514 aids in many ways including, but not limited to, maintaining the integrity of the catheter assembly 510 prior to insertion into a patient and preventing unintentional needle sticks and packaging damage (where non-rigid embodiments of the packaging is used). In the exemplary embodiment, the connective portion 516 includes spring-like connective properties such that the protective sheath 504 may be removed by applying force to the pull tab 512. In the exemplary embodiment, the catheter assembly guard 514 includes a portion to protect at least a portion of the circumference of the catheter assembly 510 and at least a portion to protect the entire circumference of the distal end of the catheter assembly 510. However, in some embodiments, the protective sheath 504 may protect the entire circumference of the entire catheter assembly 510 and in still other embodiments, at least a portion, and in some embodiments, less than 100 percent, of the distal end of the catheter assembly 510 may be protected. Some embodiments of the system may not include a protective sheath. In some embodiments, a rigid packaging may be used to protect and maintain the integrity of the catheter assembly. Some embodiments of rigid packaging are described below with respect to FIGS. 13A-13B.

Referring now to FIG. 5B, a magnified sectional view of the distal portion of the catheter is shown. In the exemplary embodiment, the catheter may be a catheter similar to those shown and described above with respect to FIGS. 3B and 4B. Referring again to FIG. 5A, the device 500 includes the position tab 520 to maintain the position of the catheter 518 with respect to the introduction needle.

Referring to FIG. 5C, the device 502 is shown in the locked position, the top portion 506 having traveled the full distance. The locking mechanism 522 is shown and is in the locked position, having been released when the clip 524 reached the back of the flash member as the top portion 506 reached the full distance of travel with respect to the base portion 508. In this figure, the introduction needle is not shown as it is masked by the top portion 506. In this position, the top portion 506 provides protection from for the sharp introduction needle to prevent unintentional puncturing or piercing by the introduction needle. The catheter 518 has been removed from the top portion 506 of the device, and in practice, the catheter 518 would be removed after it is positioned in the patient.

In the exemplary embodiment shown in FIGS. 5A-5C, when in a fully assembled unlocked position, i.e., similar to that shown in FIG. 5A with the protective sheath 504 attached to the device 502, the device may measure about 4.512 inches in length. The distance between the top edge of the catheter assembly guard 514 and the top edge of the pull tab 512 may measure about 0.901 inches. The width of the fully assembled device at the point of attachment of the protective sheath 504 on the base portion 508 may measure about 0.385 inches. In the exemplary embodiment, the angle formed between the top edge of the catheter assembly guard 514 and the sheath portion between the catheter assembly guard 514 and the pull tab 512 may be about 19 degree. These measurements are approximate and serve only as example of an exemplary embodiment. Various embodiments may include various measurements that may be greater or less than those given above.

Figure 6A:
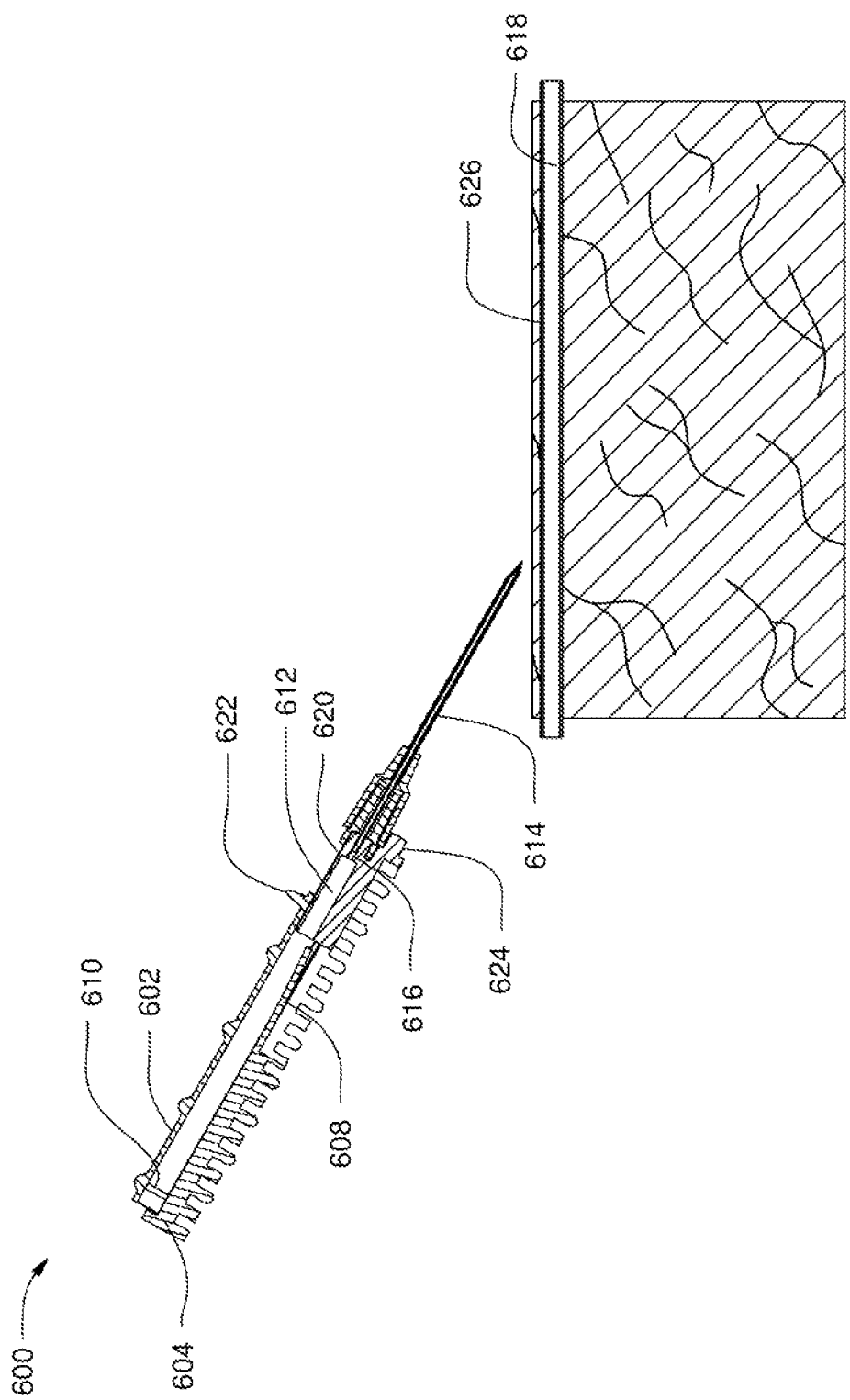
FIGS. 6A-6H are illustrated, sequential views of the device in practice, according to one embodiment.
Figure 6B:
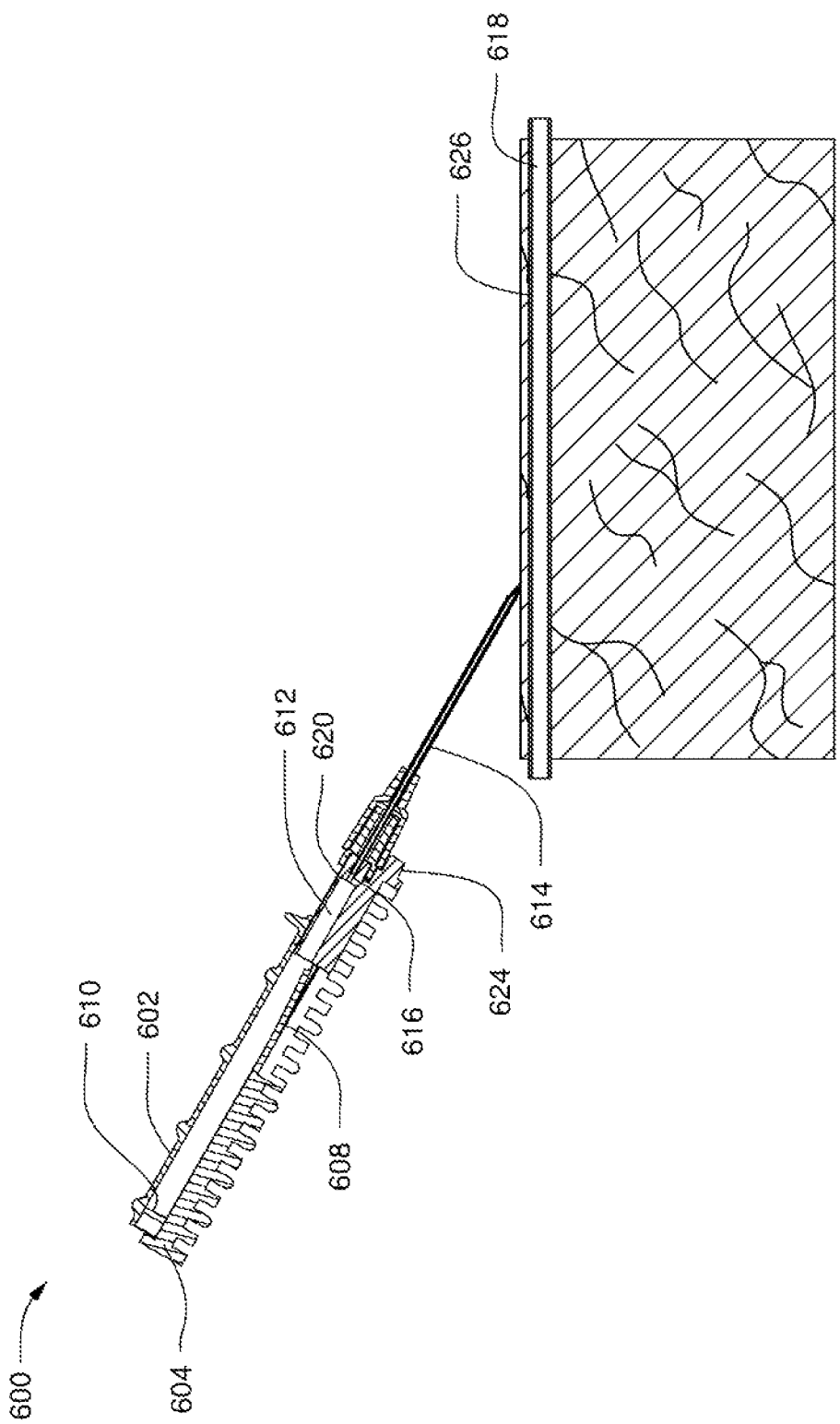
Figure 6C:
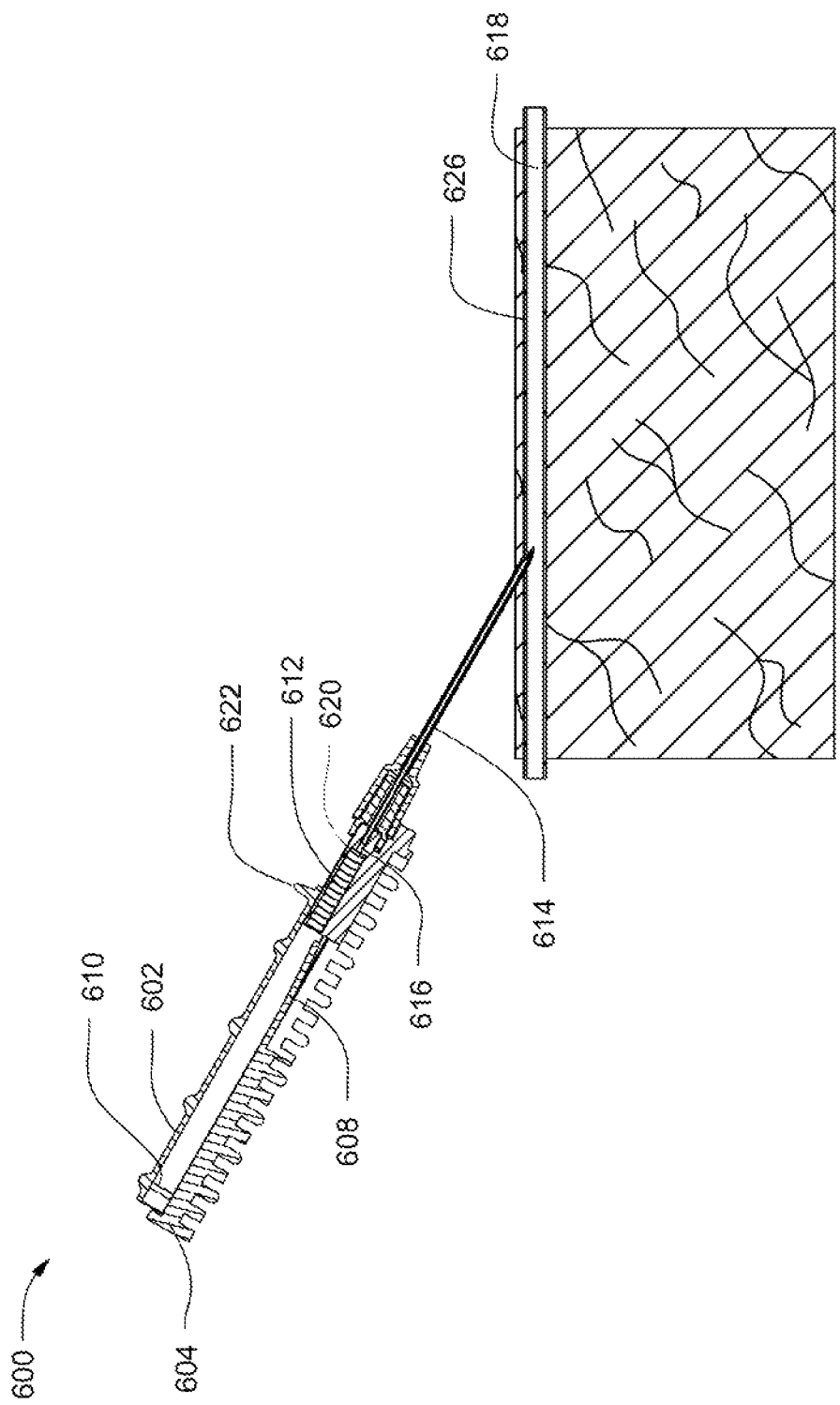

Referring now to FIGS. 6A-6F, in practice, the device 600 may be used to insert a catheter 614 into a vein 618 of a patient. FIGS. 6A-6F present a step-by-step illustration of the system, methods and apparatus of the exemplary embodiment. Referring first to FIG. 6A, the device 600 is in the unlocked and starting position. The catheter 614 is outside of the vein 618 and the patient's skin 626. The introduction needle 616 is inside the catheter 614. The position tab 624 maintains the catheter 614 in the ideal clock position with respect to the needle 616. The flash chamber 612 is empty and the window 620 is positioned above the flash chamber 612. Referring now to FIG. 6B, the device 600, still in the locked position, progresses towards and into the patient's skin 626. Referring now to FIG. 6C, the catheter 614 and introduction needle 616 enter the vein 618, and the blood, or flash fluid, flows to the flash chamber 612, which is visible to the user through the window 620 on the top portion 602. At this point, the user may cease to advance the device 600 further towards the patient's skin 626, as advancing the entire device 600 advances the introduction needle further into the vein 618, which may be unnecessary as the catheter 614 has already entered the vein 618.

Thus, once the catheter 614 is in the vein 618, this may be confirmed by visible flash fluid in the flash chamber 612, seen through the window 620. At this time, to further advance the catheter 614, without further advancing the introduction needle 616, which, as discussed above, is unnecessary and may cause trauma to the vessel, the user, gripping the device 600 and, in some embodiments, using the thumb feature 622 on the top portion 602, which may provide for increased stability and control of the device 600, the user advances the top portion 602 toward the patient's skin 626, by sliding the top portion 602 with respect to the base portion 604.

Figure 6D:
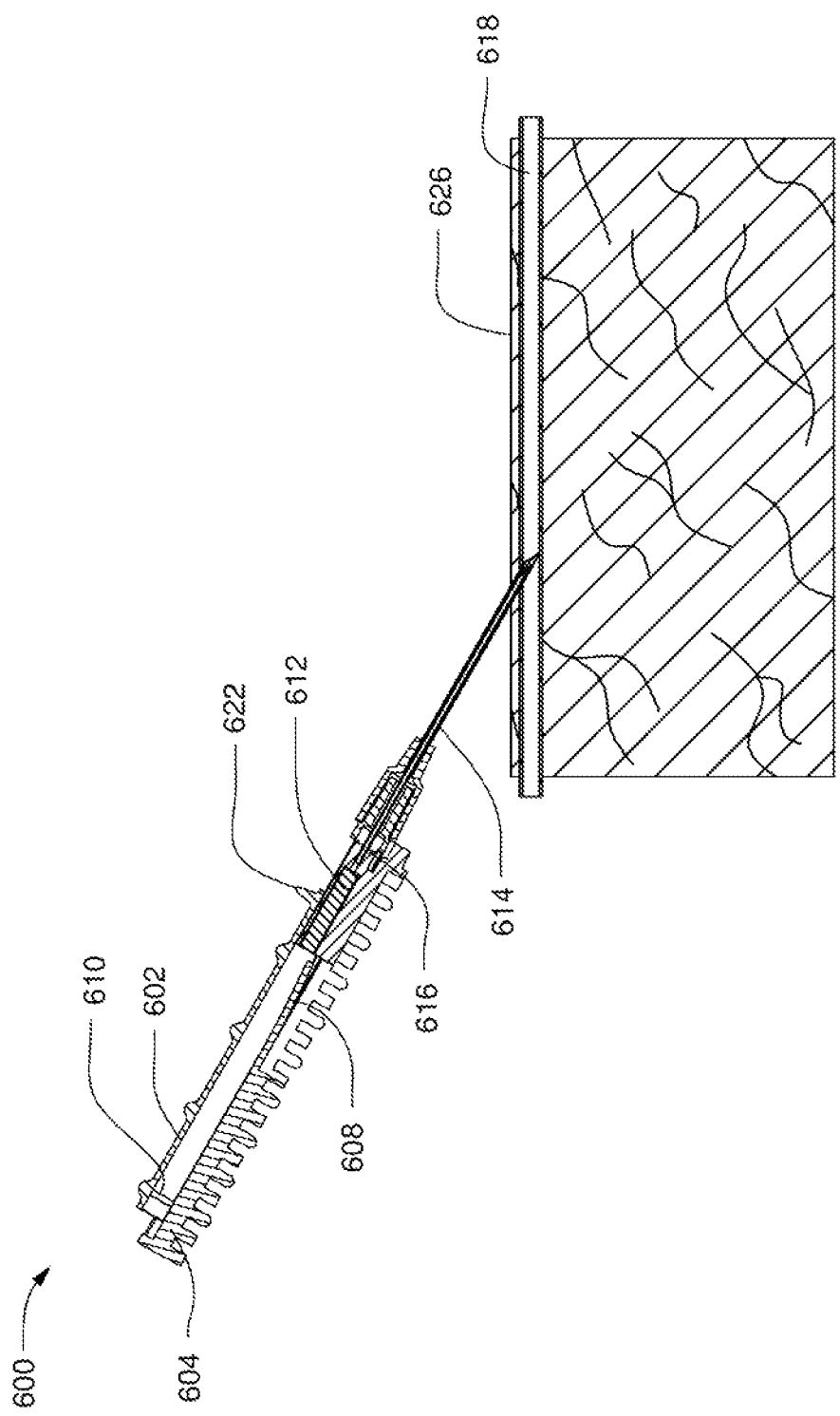

Referring to FIG. 6D, the top portion 602 has advanced towards the patient's skin, and the catheter 614 has further advanced into the vein 618. Also, the clip 610, on the top portion 602, is progressing along the locking mechanism 608, part of the base portion 604.

Figure 6E:
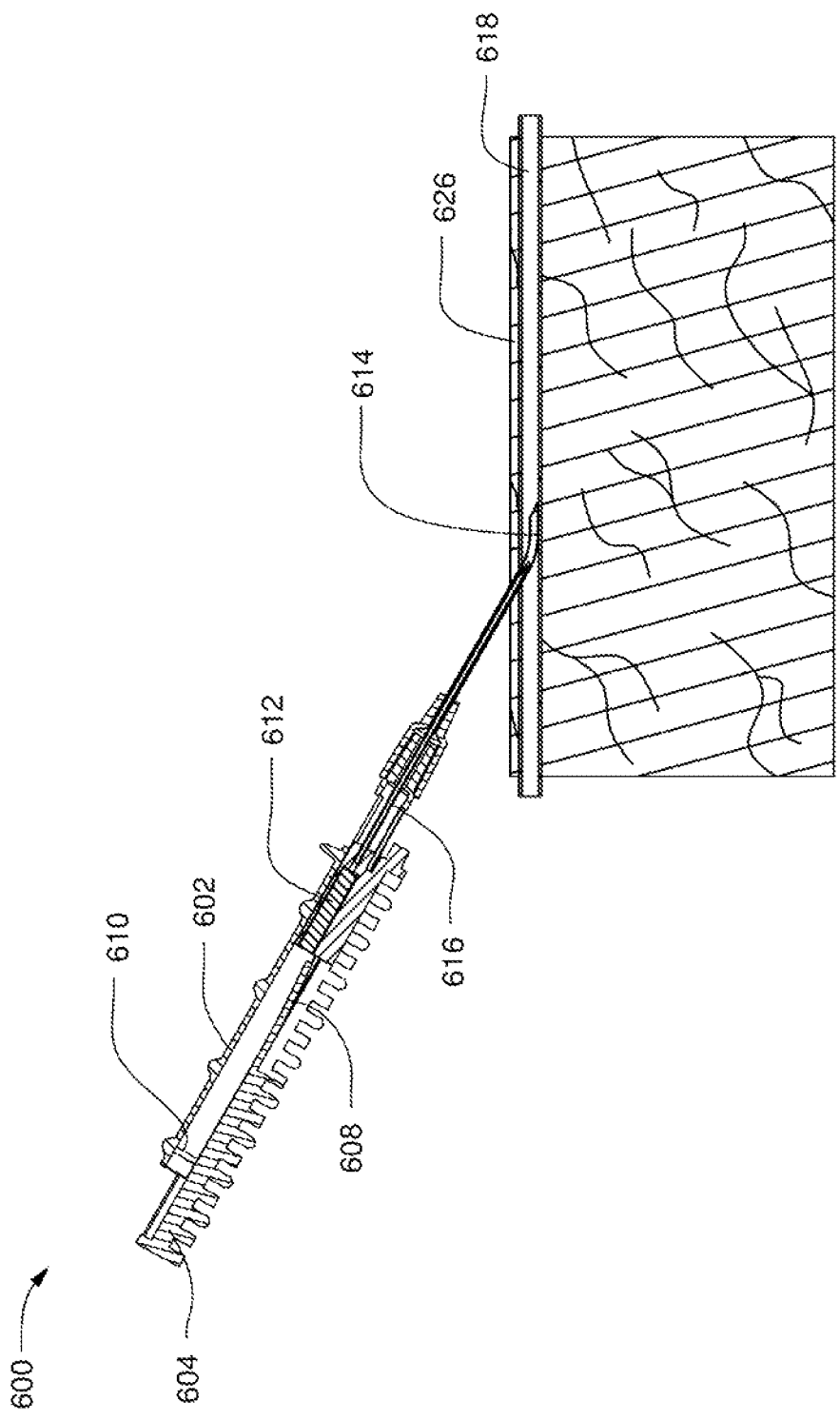
Figure 6F:
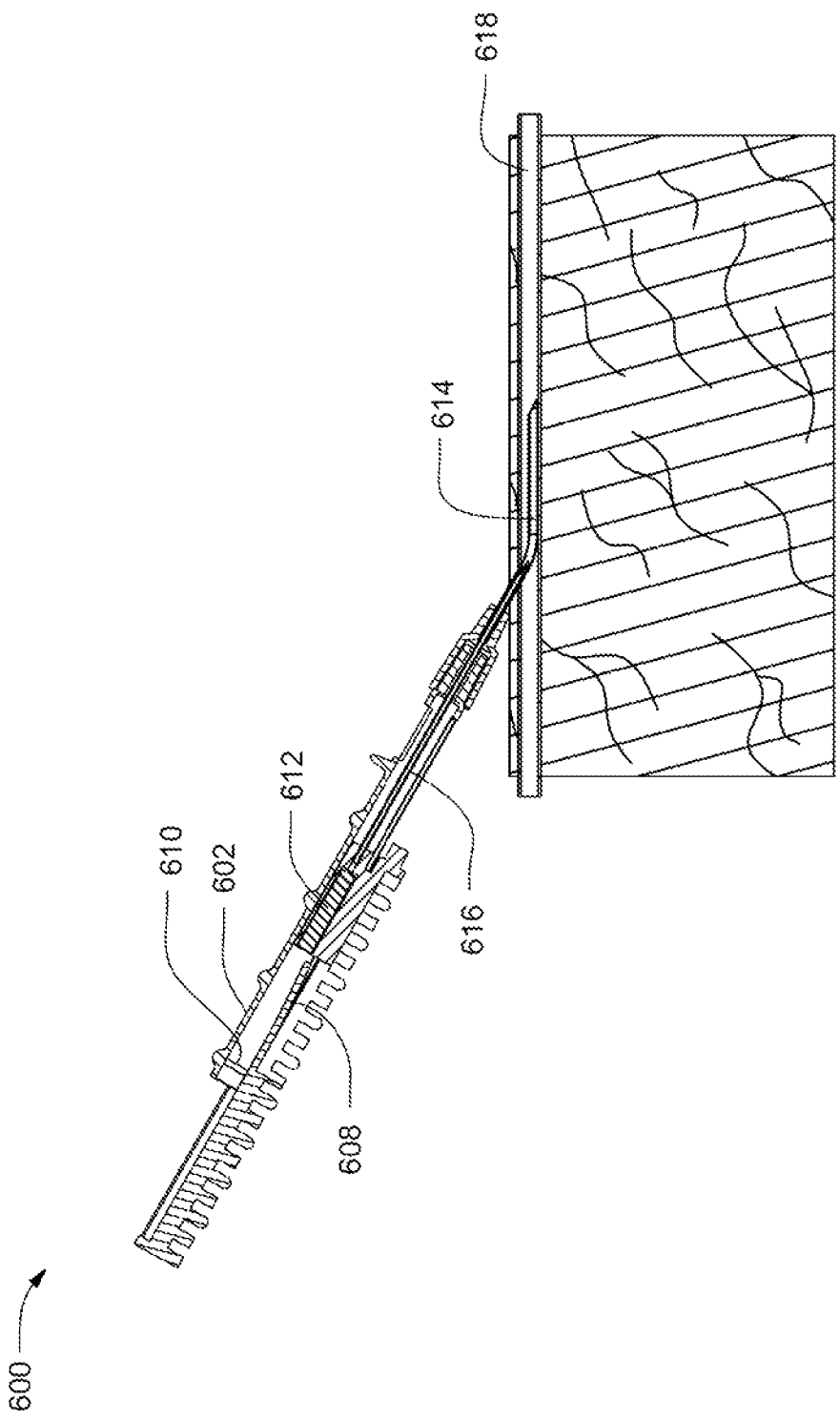
Figure 6G:
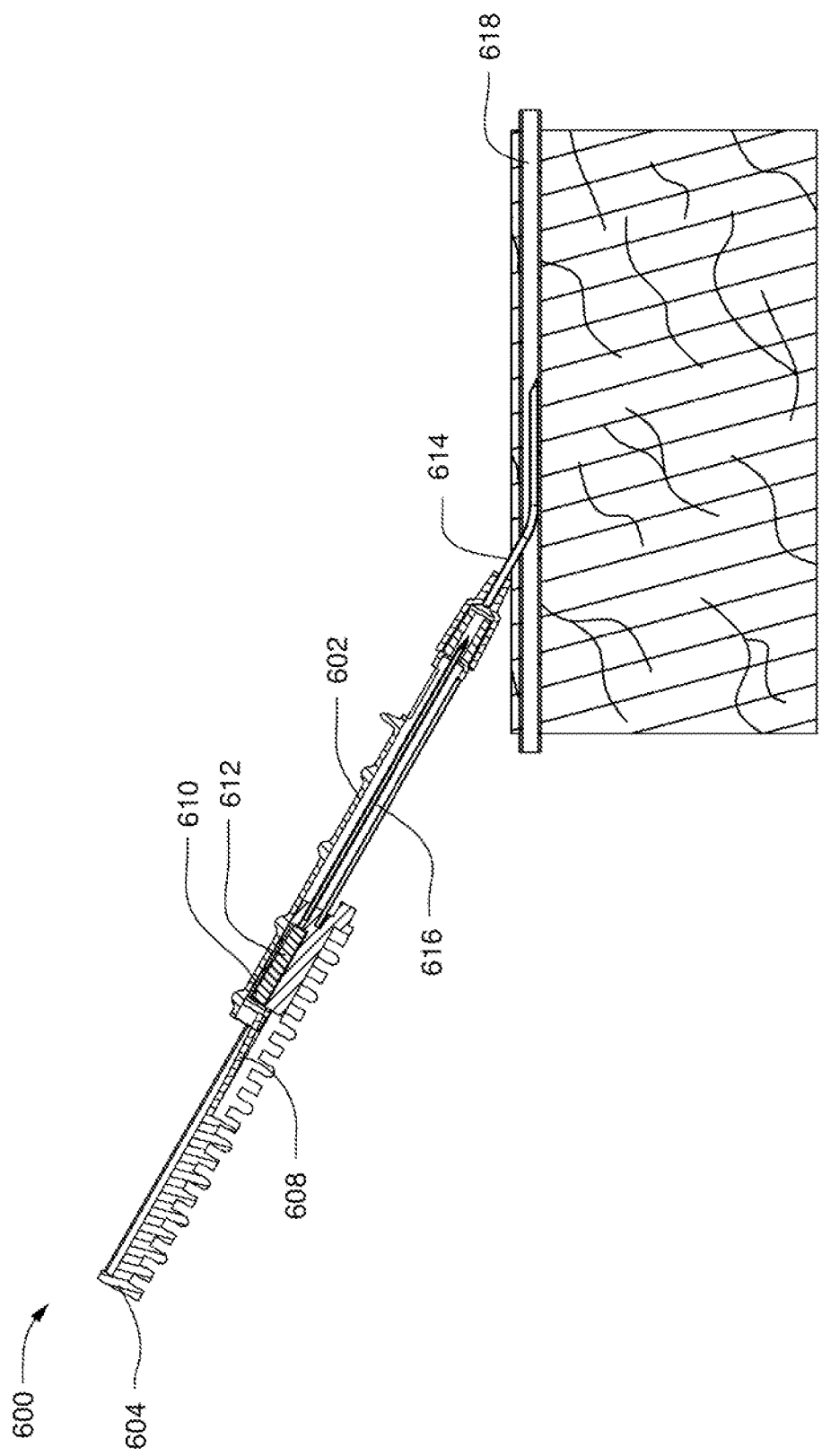
Figure 6H:
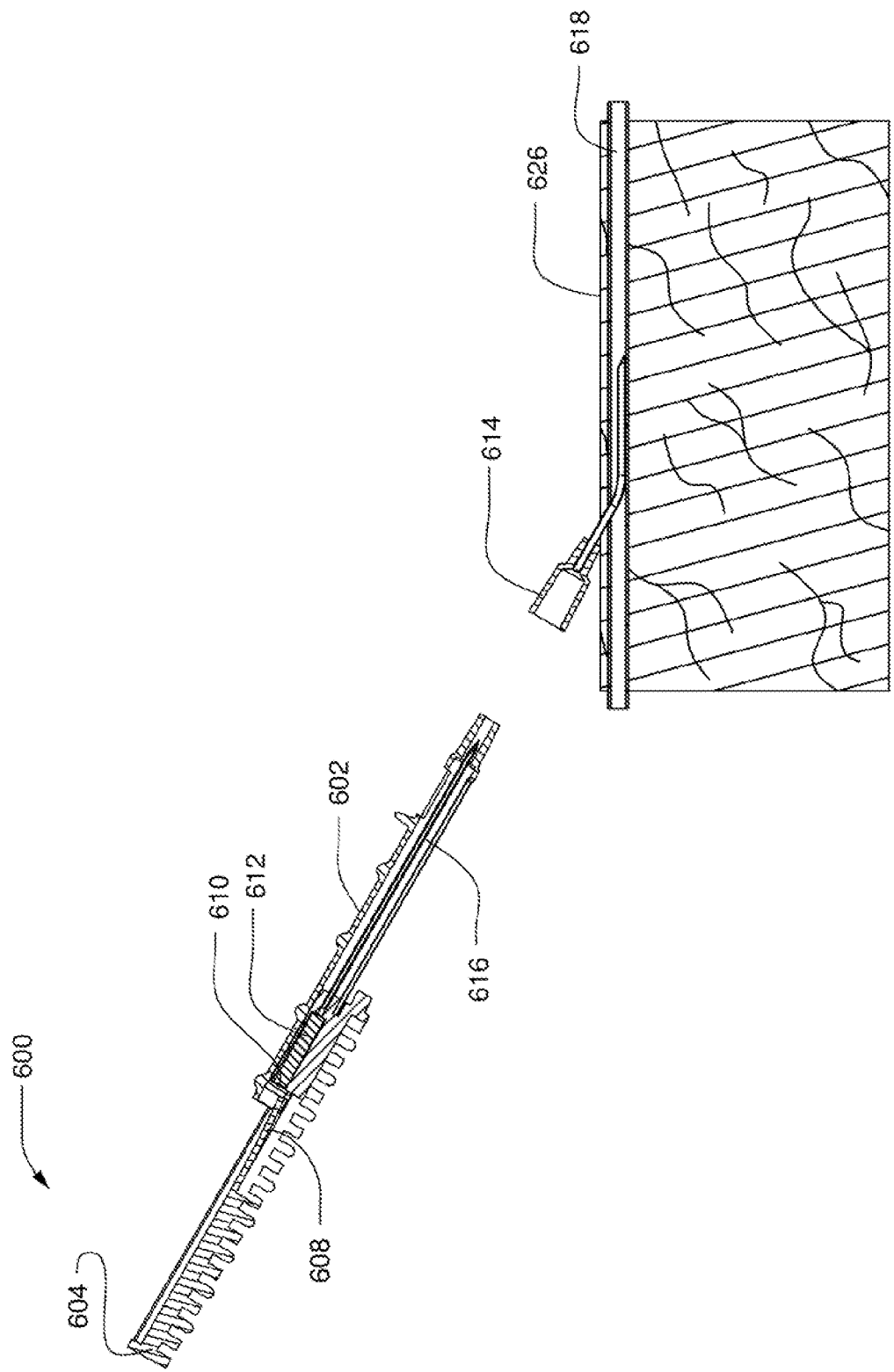

Referring to FIG. 6E, as the top portion 602 further advances towards the patient's skin 626, the top portion 602 is encapsulating additional portions of the introduction needle 616. Also, the catheter 614 is being further inserted into the vein 618. Referring now to FIGS. 6F-6G, the top portion 602 advances until the top portion 602 reaches the full distance. At this point, the catheter 614 is fully inserted into the vein 618, the introduction needle 616 is fully encapsulated by the top portion 602 and the clip 610 releases the locking mechanism 608 and the device 600 is in the locked position. In the exemplary embodiment, in the locked position, the clip 610 is located between the flash chamber 612 and the locking mechanism 608. The position of the locking mechanism 608 prevents the top portion 602 from sliding backwards. Thus, the top portion 602 being locked in position; the top portion 602 provides a secure container for the introduction needle 616. Referring now to FIG. 6H, as discussed above, in the exemplary embodiment, the catheter 614 is removably attached to the top portion 602. Once the catheter 614 has been successfully inserted into the vein 618, by moving the device away from the patient's skin, the catheter 614 may easily become separate from the device 600.

Figure 7:
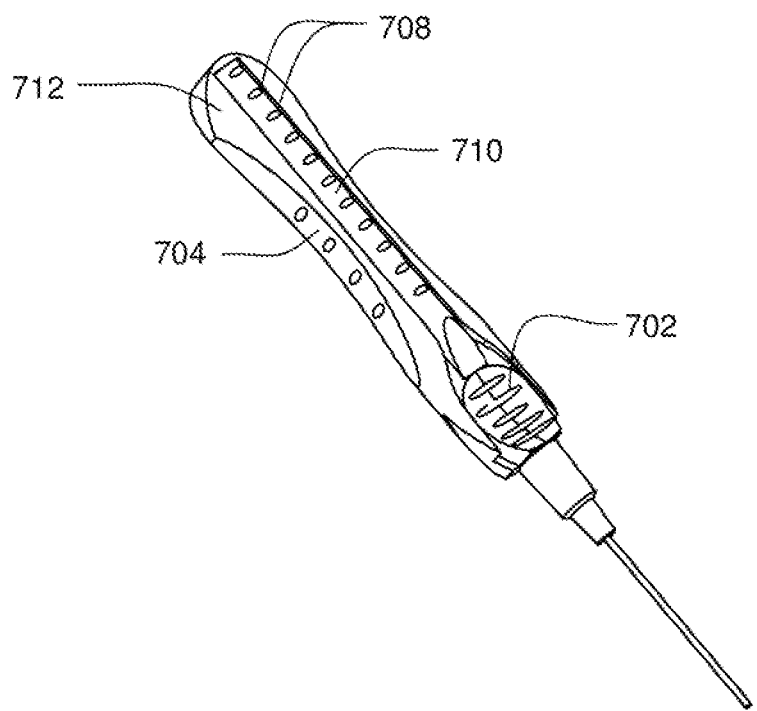
FIG. 7 is a view of one embodiment of the device.
Figure 8A:
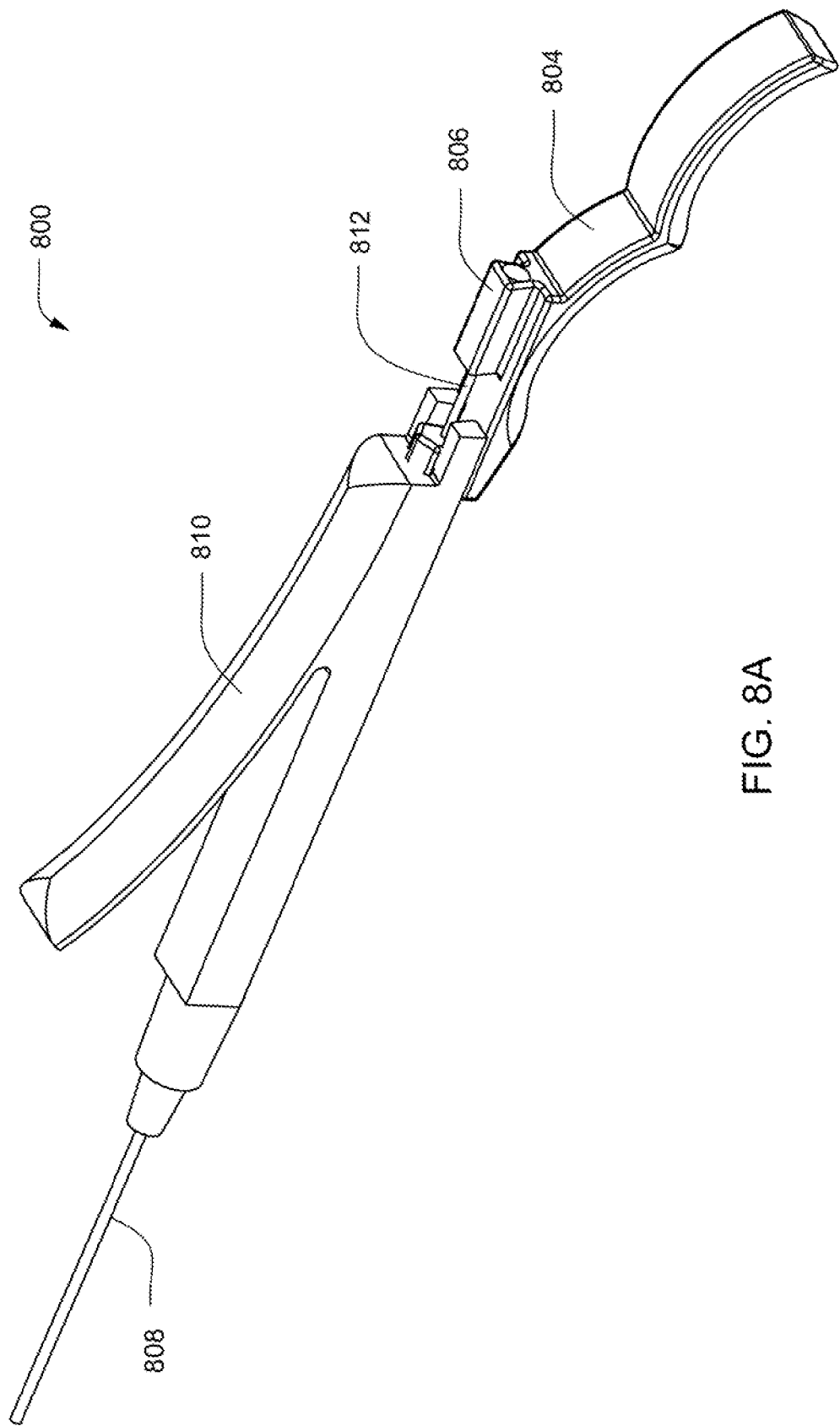

Although an exemplary embodiment of the device has been described herein, various other embodiments of the device may include one or more features described herein with respect to the exemplary embodiment, however, the device may include additional feature and/or include alternate embodiments of one or more features described above with respect to the exemplary embodiment. Referring to FIG. 7, another embodiment of the insertion device 700 is shown. One or more contouring features of the device 700 may be used in various embodiments of the exemplary embodiment. For example, in some embodiments, it may be desirable to include one or more of the following features: a depressed thumb feature 702, one or more side cut features 704, and rib structures 706, or a raised centered rib feature along at least part of the length of the top portion 712, such as those shown on the device 700.

Referring now to FIGS. 8A-8D, another embodiment of the insertion device is shown. In this embodiment, the top portion 802 includes a thumb feature 810 and the base portion 804 includes ergonomic finger contours for gripping the device. In this embodiment, the flash chamber 806 slides together with the introduction needle 812 into the device 800. In this embodiment, the thumb feature 810 may be used to advance the catheter 808 off the introduction needle 812 when the user sees the flash fluid in the flash chamber 806. The flash chamber 806 may be visible through a transparent feature or an opening (not shown) in the top portion 802

Figure 9A:
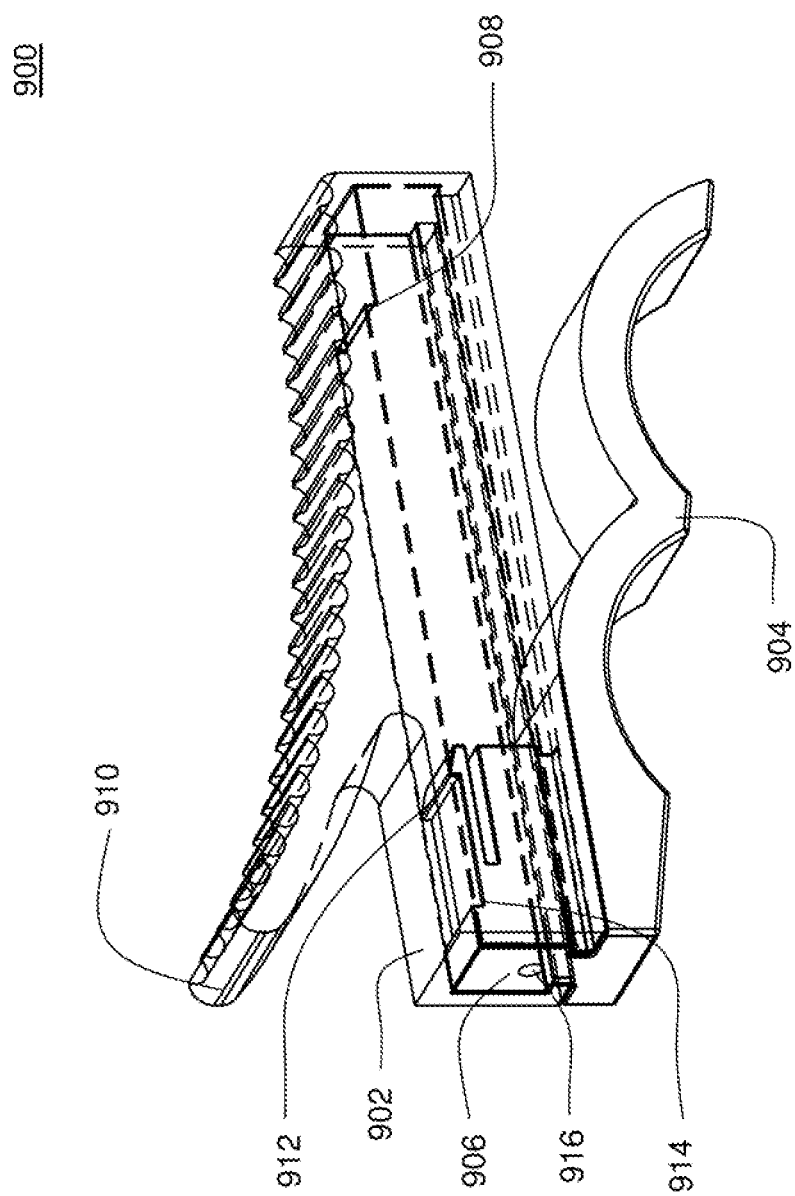
FIG. 9A is a view of one embodiment of the device in the unlocked position.
Figure 9B:
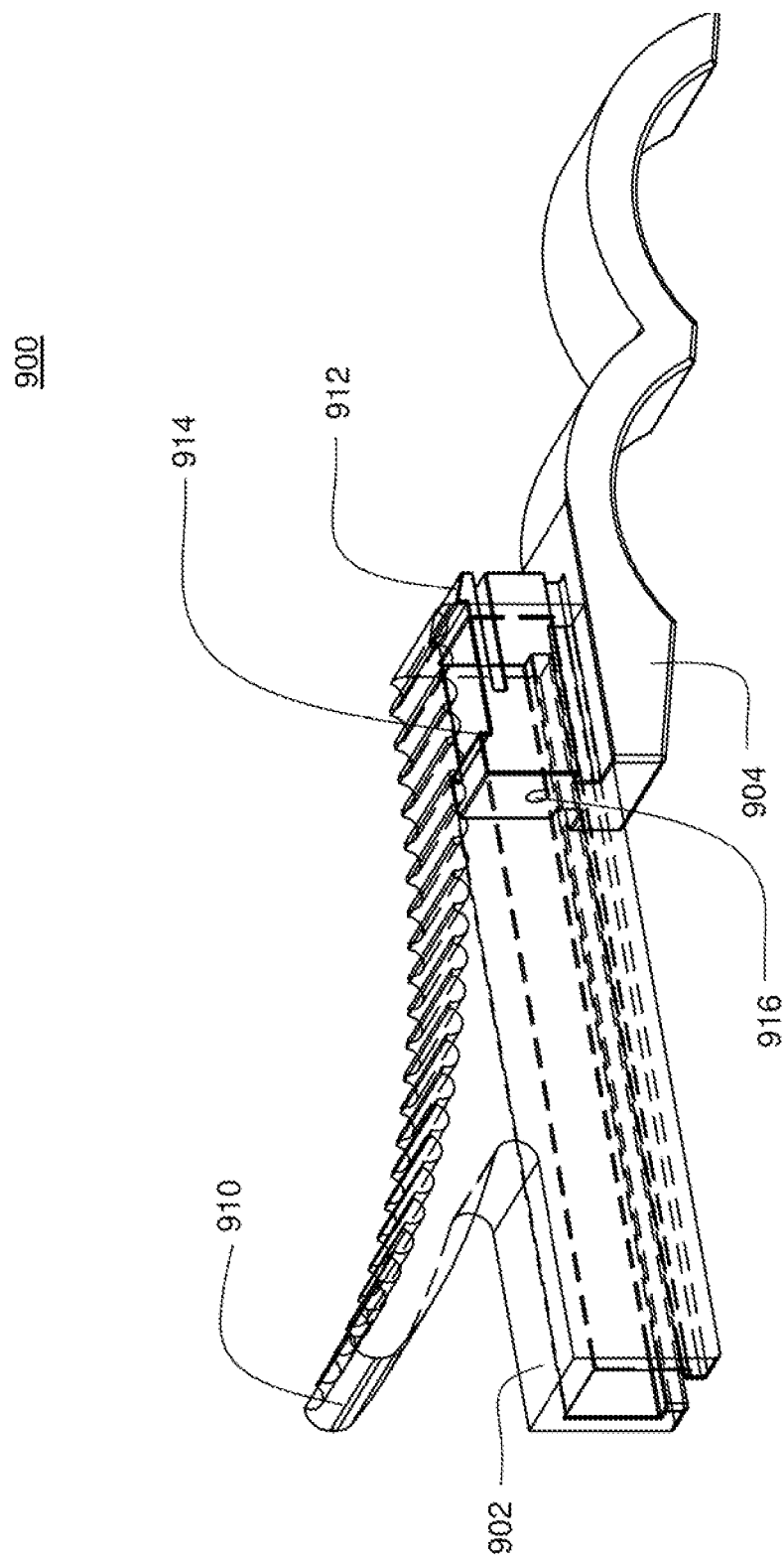
FIG. 9B is a view of the embodiment of the device shown in FIG. 9A in the unlocked position.

Referring now to FIGS. 9A and 9B, another embodiment of the insertion device is shown. Referring first to FIG. 9A, the device 900 is in an unlocked position. The top portion 902 includes a thumb feature 910 which includes, in this embodiment, a series of ridges along the surface. As discussed above, the top portion and base portion may include one or more features to assist the user, for example, the features may increase the gripping, stability, and for comfort, of the user. However, additional features may be used and may assist the user in one or more ways, including, but not limited to, the traits discussed herein. The flash chamber 906 (not visible but inside the feature 906) may be visible through a transparent feature or an opening (not shown) in the top portion 902. The flash chamber 906 is connected to the base portion 904. The flash chamber 906 includes a travel stop 914 and a locking mechanism 912. The top portion 902 slides forward with respect to the base portion 904 using a relief-and-protrusion type mechanism. The flash chamber 906 remains in position. The top portion 902 travels to full distance when the travel stop feature 908 on the top portion 902 reaches the travel stop feature 914 of the base portion 904. The locking mechanism 912 prevents the top portion 902 from sliding towards the start position. Referring to FIG. 9B, the device 900 is shown in the locked position. Although not shown in FIGS. 9A and 9B, an introduction needle may attach to the flash chamber 906 through opening 916. In the locked position, the device 900 fully encapsulates the introduction needle as the introduction needle will be inside the top portion 902.

In the embodiment shown in FIGS. 9A-9B, the top portion 902 and the flash chamber 906 are a square or rectangular shape. In this embodiment, the base portion 904 includes ergonomic finger contours for gripping the device 900. The various embodiments of the device described herein are not limited to the shapes shown in any one embodiment, features and shapes from one embodiment shown may be combined with one or more features and shapes from one or more embodiments shown to create another embodiment.

Figure 10A:
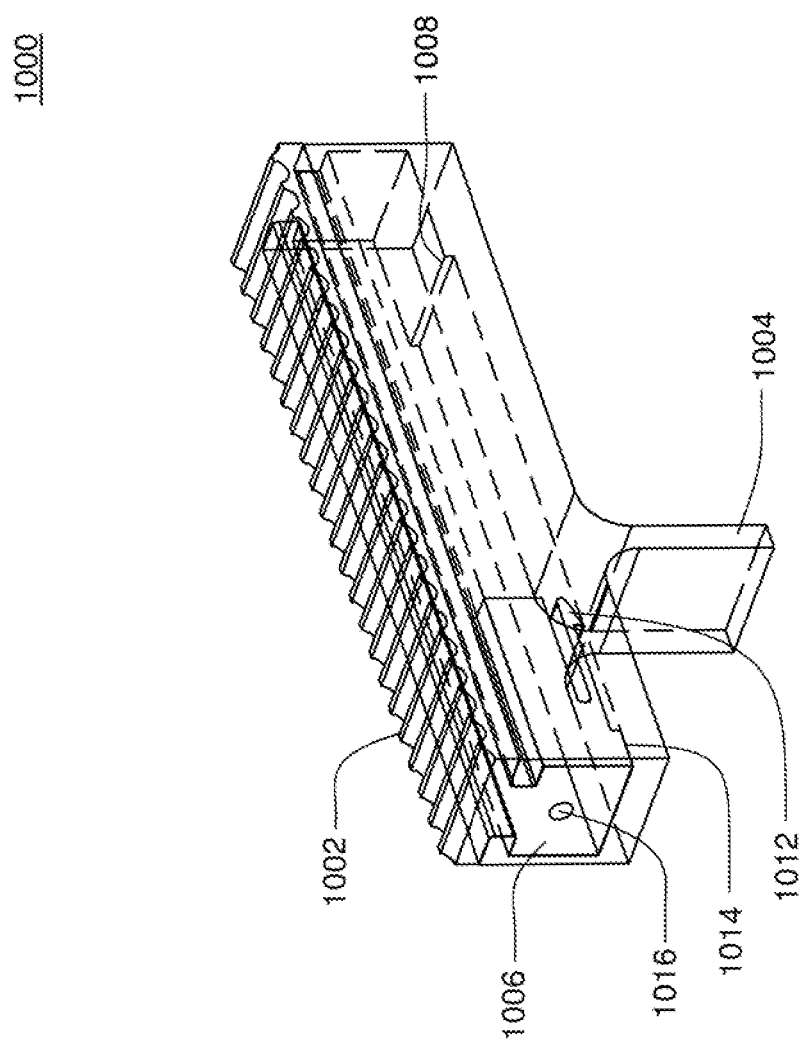
FIG. 10A is a view of one embodiment of the device in the unlocked position.
Figure 10B:
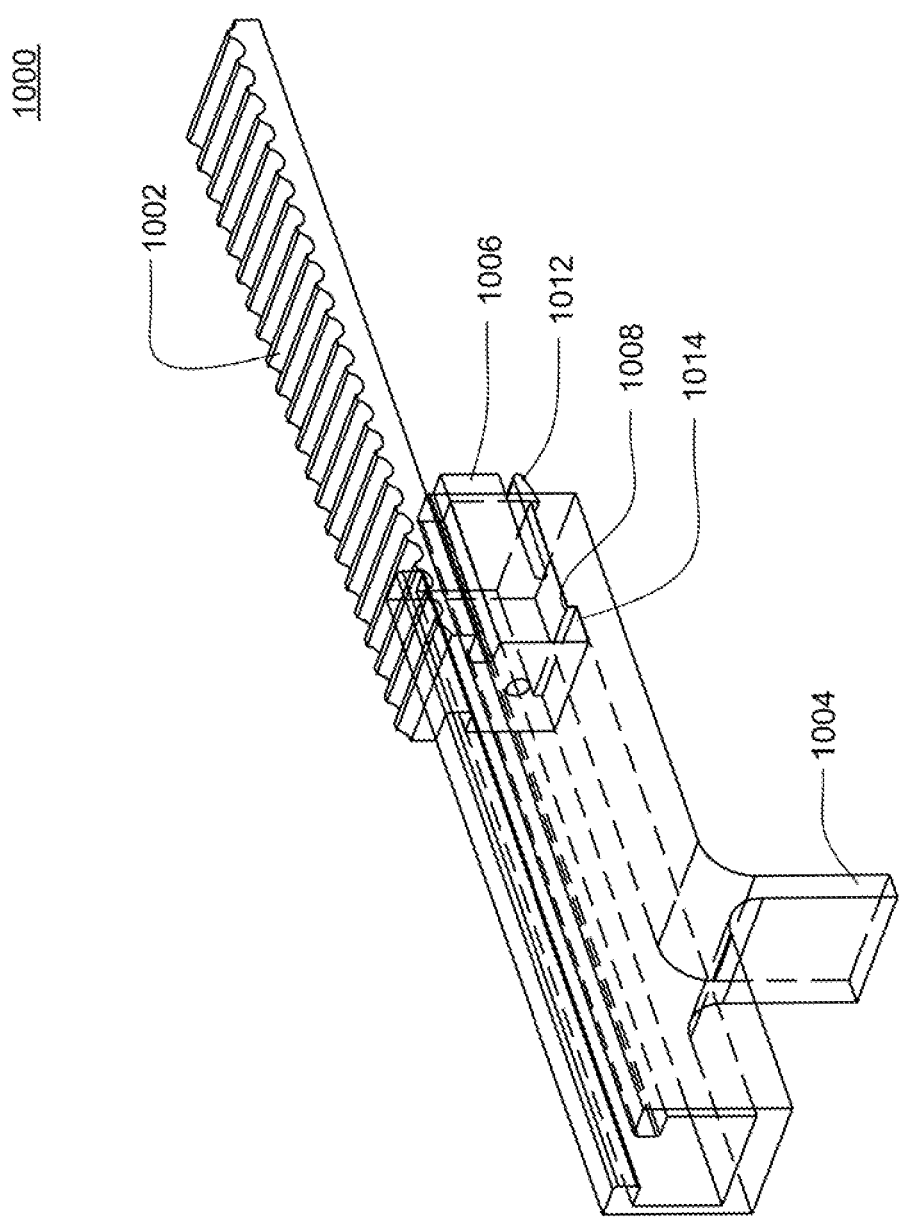
FIG. 10B is a view of the embodiment of the device shown in FIG. 10A in the unlocked position.

Referring now to FIGS. 10A and 10B another embodiment of the insertion device is shown. Referring first to FIG. 10A, the device 1000 is in an unlocked position. The top portion 1002 includes a series of ridges along the surface. As discussed above, the top portion 1002 and/or the base portion may include one or more features to assist the user, for example, the features may increase the gripping, stability, and/or comfort, of the user. However, additional features may be used and may assist the user in one or more ways, including, but not limited to, the traits discussed herein. The flash chamber 1006 (not visible but inside the feature 1006) may be visible through a transparent feature or an opening (not shown) in the top portion 1002. The flash chamber 1006 is connected to the top portion 1002. The flash chamber 1006 includes a travel stop 1014 and a locking mechanism 1012. The embodiment shown in FIGS. 10A and 10B is essentially an inverted version of the embodiment shown in FIGS. 9A and 9B, wherein the travel stop features 1014, 1008 are located on the bottom of the flash chamber 1006, rather than on the top, as shown in FIGS. 9A and 9B. Additionally, the flash chamber 1006 is connected to the top portion 1002 in the embodiment shown in FIGS. 10A and 10B, rather than the base portion, as is the case in the embodiment shown in FIGS. 9A and 9B (device 900).

Still referring to FIGS. 10A and 10B, the top portion 1002, together with the flash chamber 1006, slides backward with respect to the base portion 1004 using a relief-and-protrusion type mechanism. The top portion 1002 travels to full distance when the travel stop feature 1014 on the top portion 1002 reaches the travel stop feature 1008 of the base portion 1004. The locking mechanism 1012 prevents the top portion 1002 from sliding towards the start position. Referring to FIG. 10B, the device 1000 is shown in the locked position. Although not shown in FIGS. 10A and 10B, an introduction needle may attach to the flash chamber 1006 through opening 1016. In the locked position, the device 1000 fully encapsulates the introduction needle as the introduction needle will be inside the top portion 1002.

In the embodiment shown in FIGS. 9A-9B, the top portion 902 and the flash chamber 906 are a square or rectangular shape. In this embodiment, the base portion 904 includes ergonomic finger contours for gripping the device 900. The various embodiments of the device described herein are not limited to the shapes shown in any one embodiment, features and shapes from one embodiment shown may be combined with one or more features and shapes from one or more embodiments shown to create another embodiment.

Figure 11A:
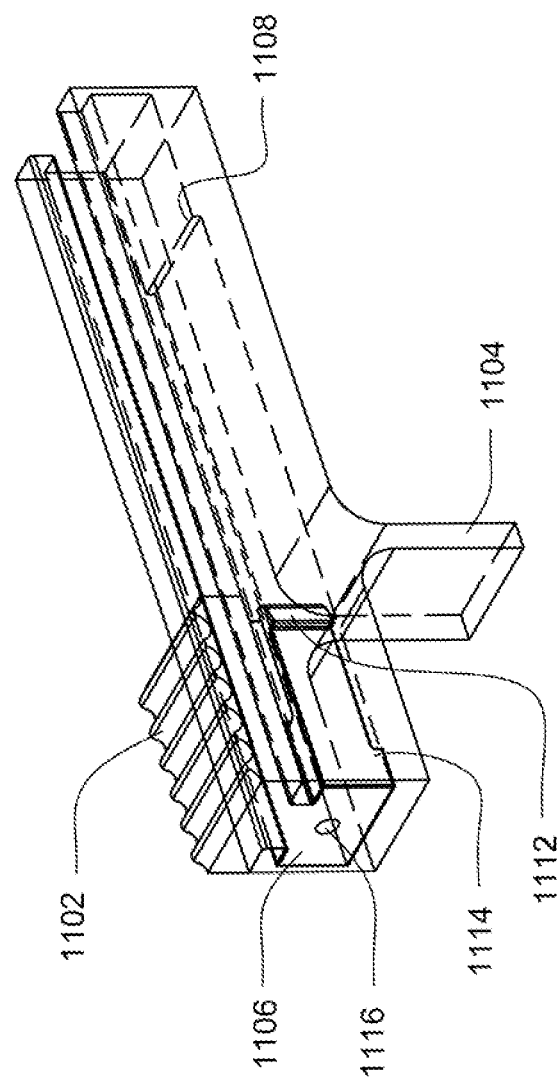
FIG. 11A is a view of one embodiment of the device in the unlocked position.
Figure 11B:
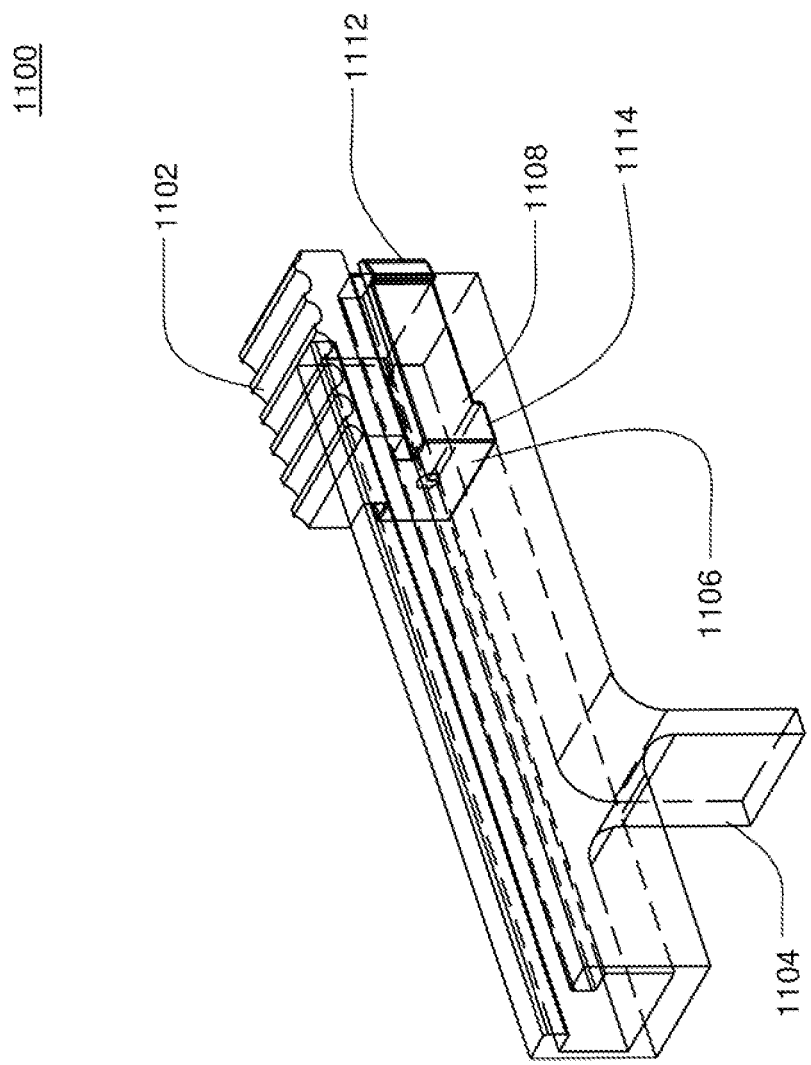
FIG. 11B is a view of the embodiment of the device shown in FIG. 11A in the unlocked position.

Referring now to FIGS. 11A and 11B, another embodiment of the insertion device is shown. Referring first to FIG. 11A, the device 1000 is in an unlocked position. The top portion 1102 includes a series of ridges along the surface. As discussed above, the top portion 1102 and/or the base portion may include one or more features to assist the user, for example, the features may increase the gripping, stability, and/or comfort, of the user. However, additional features may be used and may assist the user in one or more ways, including, but not limited to, the traits discussed herein. In the embodiments shown in FIGS. 11A and 11B, the top portion 1102 is cropped as compared with the top portion 1002 shown in FIGS. 10A and 10B. In some embodiments, it may be desirable to have a shorter length top portion 1002 (or bottom portion). In the embodiment shown in FIGS. 11A and 11B, the length of the top portion 1102 may reduce the total weight of the device and may require less material to manufacture, both of which may be desirable and/or advantageous.

The flash chamber 1106 (not visible but inside the feature 1106) may be visible through a transparent feature or an opening (not shown) in the top portion 1102. The flash chamber 1106 is connected to the top portion 1102. The flash chamber 1106 includes a travel stop 1014 and a locking mechanism 1012. The embodiment shown in FIGS. 11A and 11B is similar to the embodiment shown in FIGS. 10A and 10B, wherein the travel stop features 1114, 1108 are located on the bottom of the flash chamber 1106, rather than on the top, as shown in FIGS. 9A and 9B. Additionally, the flash chamber 1106 is connected to the top portion 1102 in the embodiment shown in FIGS. 11A and 11B, rather than the base portion, as is the case in the embodiment shown in FIGS. 9A and 9B (device 900).

Still referring to FIGS. 11A and 11B, the top portion 1102, together with the flash chamber 1106, slides backward with respect to the base portion 1104 using a t relief-and-protrusion type mechanism. The top portion 1102 travels to full distance when the travel stop feature 1114 on the top portion 1102 reaches the travel stop feature 1108 of the base portion 1104. The locking mechanism 1112 prevents the top portion 1102 from sliding towards the start position. The locking mechanism 1112 in FIGS. 11A and 11B is located on the side of the flash chamber 1106 rather than the bottom or top of the flash chamber, as shown in the embodiments shown in FIGS. 9A-10B. Referring to FIG. 11B, the device 1100 is shown in the locked position. Although not shown in FIGS. 11A and 11B, an introduction needle may attach to the flash chamber 1106 through opening 1116. In the locked position, the device 1100 fully encapsulates the introduction needle as the introduction needle will be inside the top portion 1102.

With respect to the embodiments shown in FIGS. 10A-11B, the geometry of the base portion 1004, 1104 may be altered to accommodate all sides of the introduction needle (not shown) when in the locked position (see FIGS. 10B and 11B). Alternations may include, but are not limited to, additional length added to the base portion 1004, 1104, and including additional geometries in the base portion 1004, 1104 structure.

Figure 12:
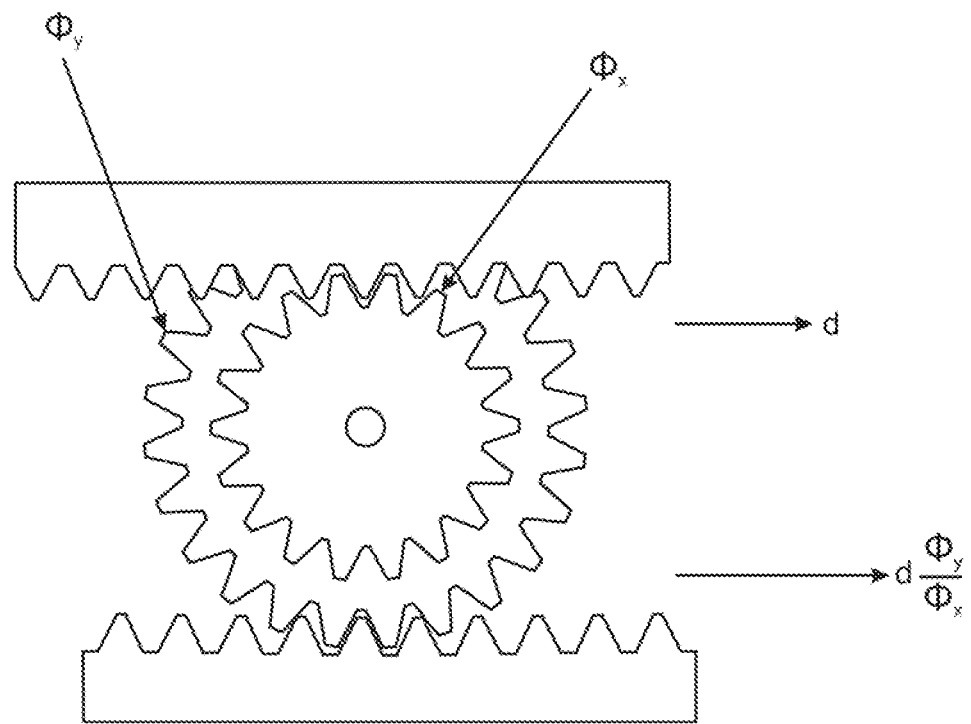
FIG. 12 is an illustrative view of one embodiment of the rack-and-pinion embodiment of the device.

Referring now to FIG. 12, in some embodiments, it may be desirable to insert a catheter, introduction needle or other medical device that may be longer than the travel distance of a typical user's thumb. For example, the various embodiments of the device described herein may be optimal for insertion of a medical device where the total travel distance of the medical device is equal to or less than the potential distance a user's thumb may slide the top portion of the insertion device. However, in embodiments where this is not the case, a rack-and-pinion mechanism may be used to extend the total distance traveled by the medical device. An example of a rack-and-pinion embodiment is shown in FIG. 12. In this embodiment, the total distance traveled by the device is a function of the $\Phi_y/\Phi_x$.

Figure 13A:
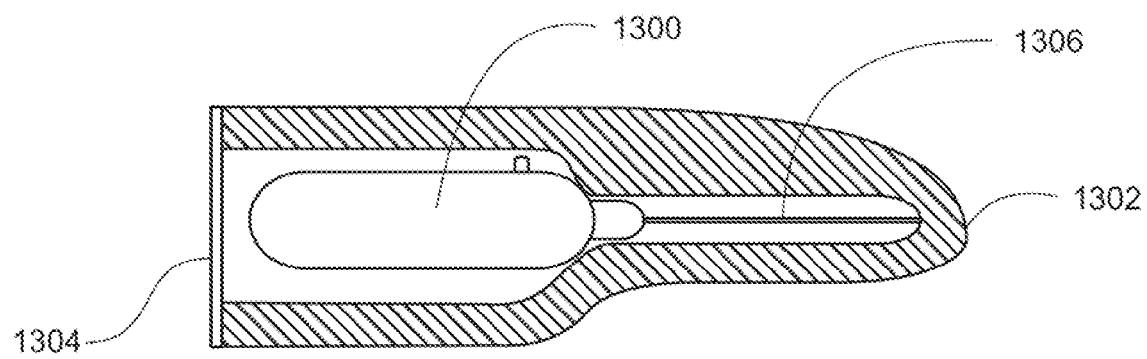
FIG. 13A is an illustrative view of one embodiment of the packaging with the device.

Referring now to FIG. 13A, one embodiment of rigid packaging for the embodiments of the device 1300 is shown. The packaging may include a rigid portion 1302, which may be made from plastic, metal or any material rigid enough to maintain the integrity of the introduction needle and catheter assembly 1306 and preventing sharps injuries, as in the exemplary embodiment, or, to maintain the integrity of the medical device assembly for insertion, in various other embodiments. The packaging may be sized and shaped to accommodate the device 1300 such that the device withstands regular shipment, packaging, storage and usage. In some embodiments, the packaging may be generally or substantially cylindrical, and in some embodiments, the rigid portion of the packaging may include contours to best accommodate the device 1300. In some embodiments, the packaging may be vacuum formed. In some embodiments, the device 1300 may be placed inside the packaging and the package may be sealed 1304 with lid stock which may be made from TYVEK or material similar to TYVEK membrane. The package may then be sterilized.

Figure 13B:
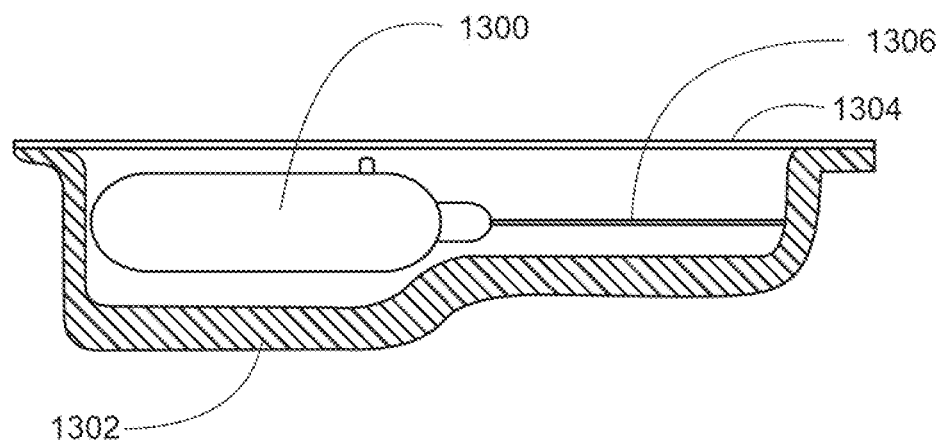
FIG. 13B is an illustrative view of one embodiment of the packaging with the device.

Referring now to FIG. 13B, in some embodiments, the packaging, as described above with respect to the packaging embodiment shown in FIG. 13A, may be shaped in any way desirable and, may be a vacuum formed tray-like packaging having a rigid portion 1302 and a non-rigid lid 1304, which may be made from lid stock which may be made from TYVEK or material similar to TYVEK membrane. The package may then be sterilized.

Referring to FIGS. 13A-13B, in use, the lid 1304 would be peeled away from the rigid portion of the packaging 1302. The device 1300 may be removed from the packaging.

Needle Formation

As described above, in some embodiments, a needle having tip or distal end wherein the distal end includes underside keel and a needle on the top side of the distal end. Various embodiments are described herein for forming or manufacturing the needle. However, additional variations on these embodiments may be used as well as various methods of manufacture that would be apparent from this disclosure.

In one embodiment, a mold made from graphite, may be used. The mold would include the intended shape of the distal end of the needle. Using stainless steel tubing stock, and the graphite mold, the distal ends may be weld-formed to the desired shape. Following, the distal end may be ground or machined into a sharp needle.

Figure 14A:
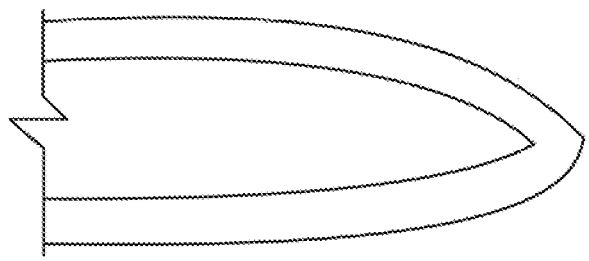
FIGS. 14A-14C are illustrative views of a method of making a needle according to one embodiment.
Figure 14B:
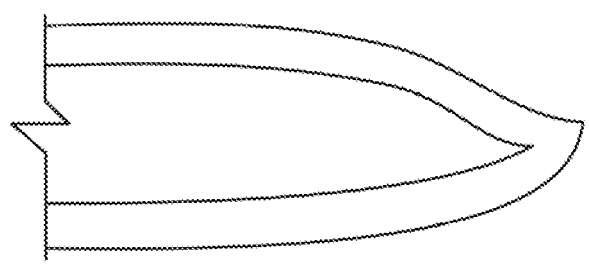
Figure 14C:
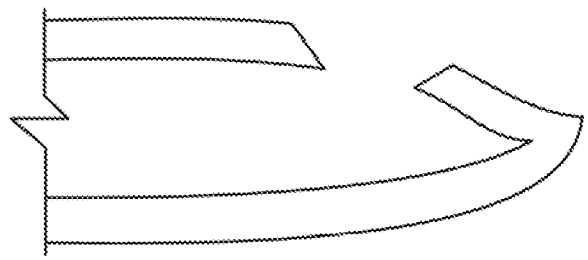
Figure 14D:
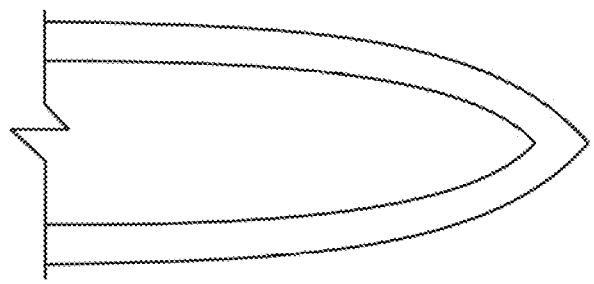
FIGS. 14D-14E are illustrative views of a technical problem according to one method of making needles.
Figure 14E:
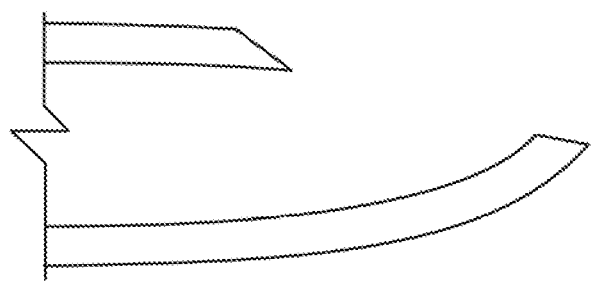
Figure 15A:
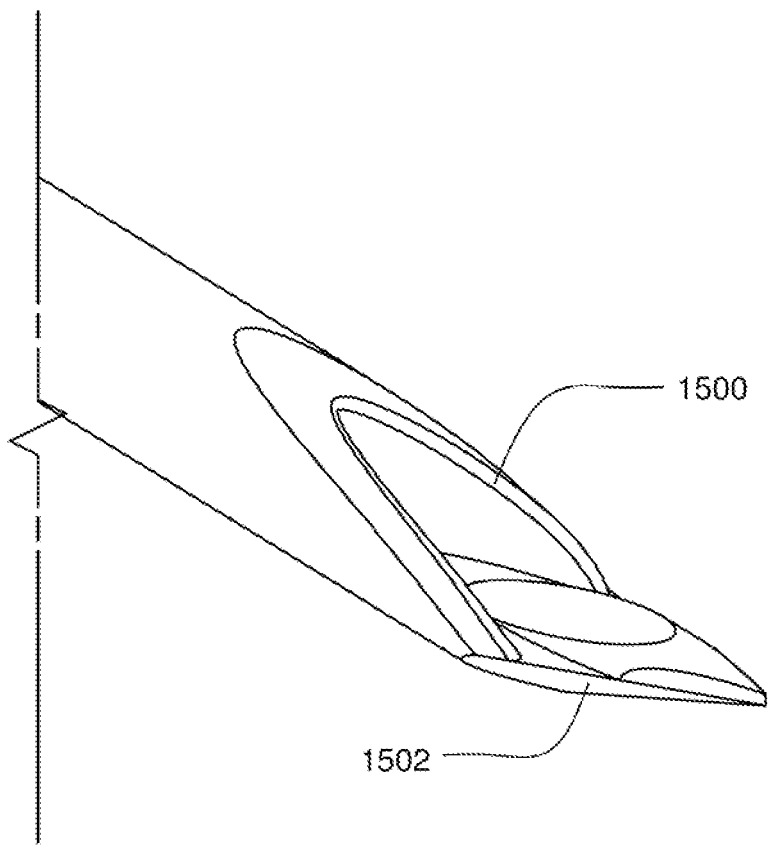
FIGS. 15A-15B are views of one embodiment of a catheter.
Figure 15B:
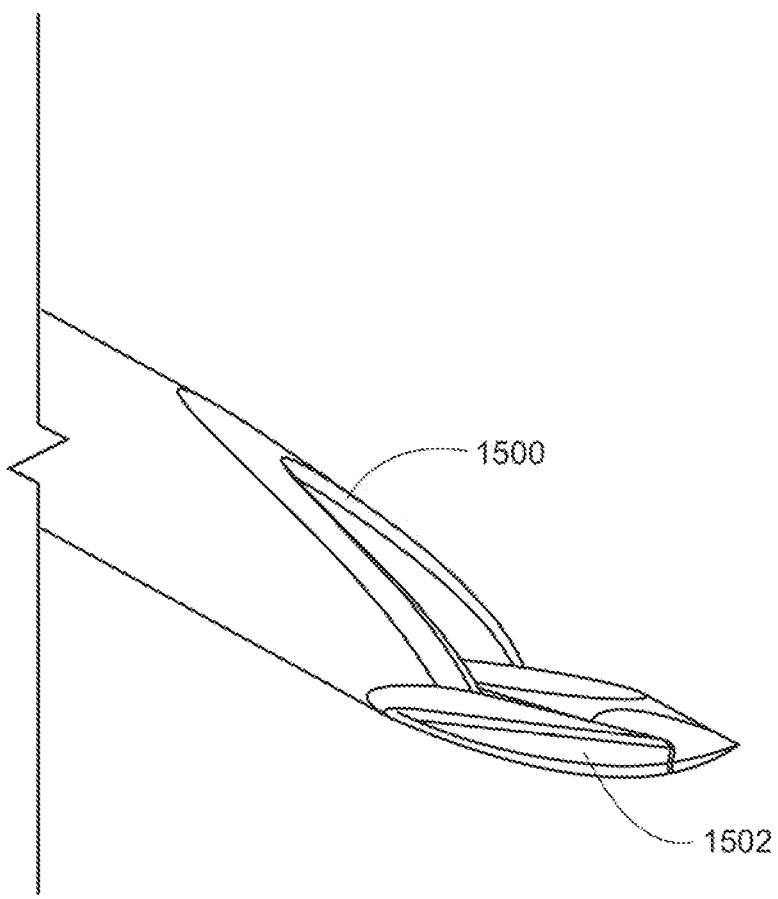
Figure 15C:
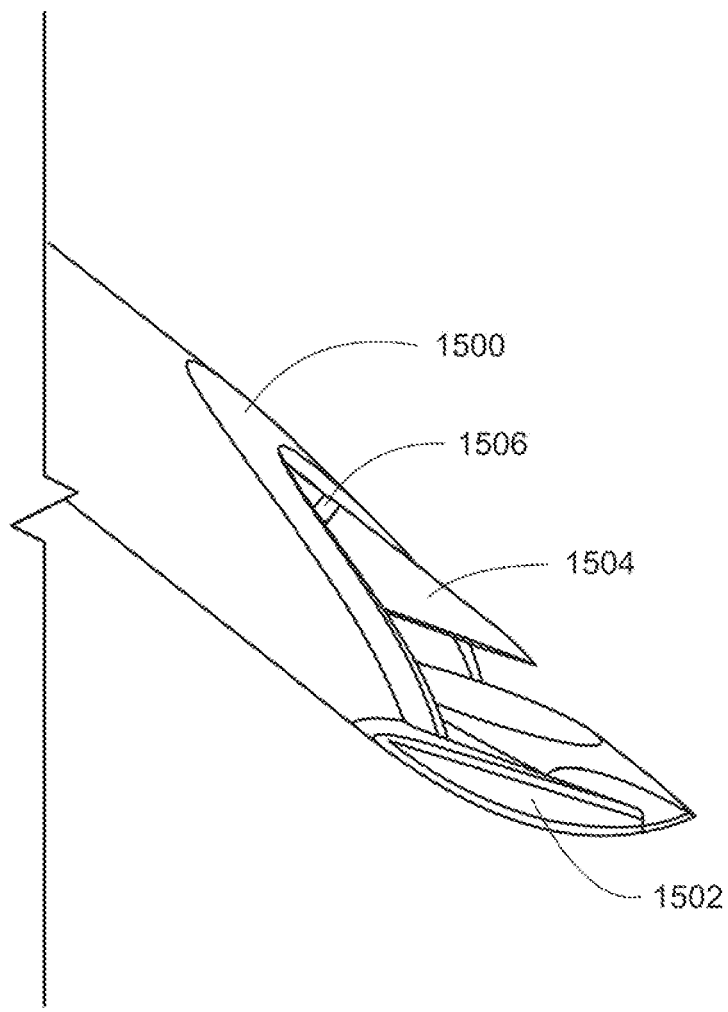
FIGS. 15C-15E are views of one embodiment of the catheter shown in FIGS. 15A-15B together with an introduction needle according to one embodiment.
Figure 15D:
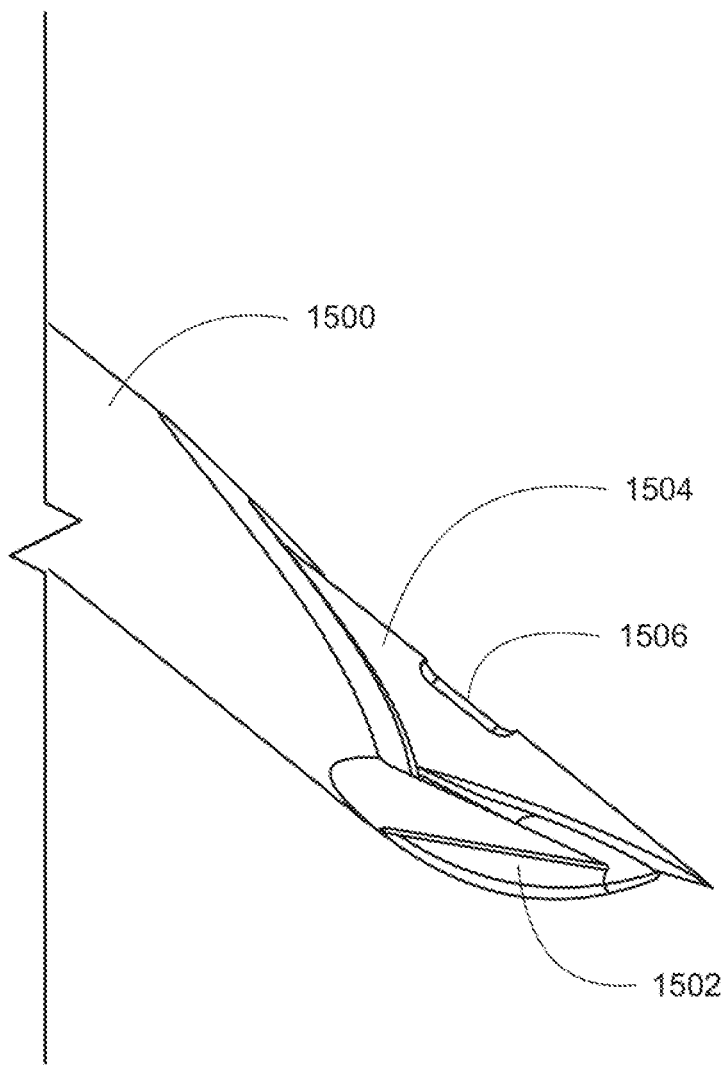
Figure 15E:
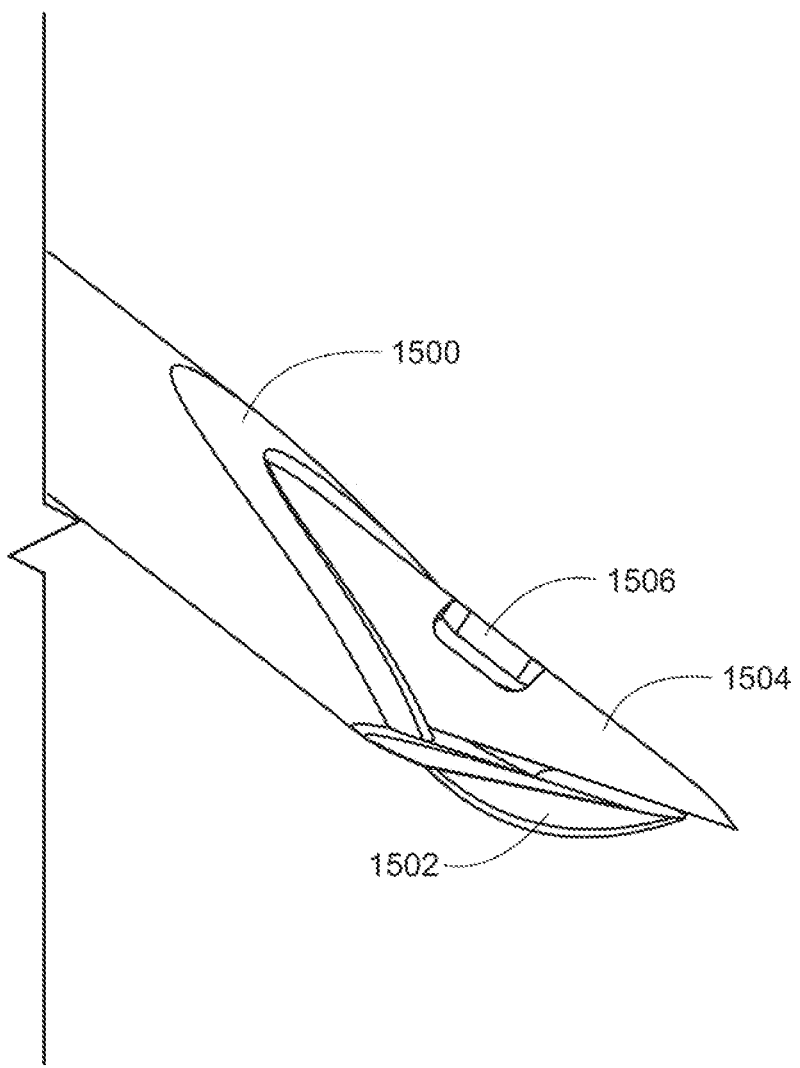

Referring now to FIGS. 14A-14C, in another embodiment, the needle tip/distal end may be formed by first using a swaging process that cold-forms, using a series of folds, the distal end of a stainless steel tube to form a needle tip. The result of this step is shown in FIG. 14A. Next, a stamping step may be used to pre-dent the swaged shape. The result of this step is shown in FIG. 14B. In this step, the top of the needle is depressed. Finally, a grinding step is used to form the needle opening/hole in the desired location. The result of this step is shown in FIG. 14C. This embodiment grinds the needle tip after a stamping step to pre-dent the swaged shape. This embodiment may have the advantage of reducing the risk of producing an unintended opening in the needle tip while grinding the needle tip following the swaging step. Grinding the tip after the stamping step to pre-dent the needle tip before grinding may reduce the risk of unintended openings in the needle tip. Referring to FIG. 14D-14E, an example of the needle tip following the swaging step is shown (FIG. 14D) as is an example of an unintended opening being formed on the needle tip where the needle tip (FIG. 14E) is ground following swaging, without the added step of stamping the needle tip following the swaging step.

Referring now to FIGS. 15A-15E, in another embodiment of making the catheter assembly, a standard point hypodermic needle 1504 is used as the introduction needle. In some embodiments, as a first step, a catheter 1500 is formed, for example, in some embodiments, having the properties described above with respect to FIGS. 3A-3B, however, in other embodiments, the catheter tip may differ. As a second step, a keel 1502 is added to the catheter 1500 tip such that the keel 1502 is added to the underside of the catheter 1500 tip. The keel 1502 essentially blocks the standard point hypodermic needle 1504 opening. However, in some embodiments, the standard point hypodermic needle 1504 opening may be sealed/plugged/filled and/or blocked with an epoxy, or other material, including, but not limited to, stainless steel or another metal, in which case welding may be used to attach the fill material. In embodiments where an epoxy is used, the epoxy may be applied into the hole, however, in some embodiments; an additional hole may be formed on the needle to mechanically hold the epoxy in the needle. However, in some embodiments, a catheter 1500 having a tip as shown in FIGS. 15A-15E may be formed as a single catheter using a molding or other process for manufacture.

In the exemplary embodiment, a new needle opening 1504 is added to the standard point hypodermic needle 1504 to serve as the needle opening in fluid communication with a flash chamber, for example, as discussed above. In the exemplary embodiment, the standard point hypodermic needle 1504 may be any standard point hypodermic needle available, including, but not limited to, the PRECISIONGLIDE by Becton Dickenson, Franklin Lakes, N.J., U.S.A., and may be selected based on the gauge and length desired for the introduction needle. In one embodiment, the standard However, in some embodiments, a needle may be manufactured to have similar characteristics to a standard point hypodermic needle, only the needle opening may be in the desired location for fluid communication with the flash chamber.

In another embodiment, starting with a standard point hypodermic needle, for example, any standard point hypodermic needle available and may be selected based on the gauge and length desired for the introduction needle, which may include the PRECISIONGLIDE by Becton Dickenson, Franklin Lakes, N.J., U.S.A., a keel may be added to the needle on the underside, which would block/plug and/or fill the standard point hypodermic needle opening. A new needle opening is then added to the top side of the needle, similar to the methods described above. The keel of the needle may be added using stainless steel or another material and may be connected to the needle by welding. However, in other embodiments, the keel may be formed using an epoxy. In those embodiments where an epoxy is used, an additional hole may be formed on the needle to mechanically hold the epoxy in the needle.

Referring now to FIGS. 16A-16C and FIGS. 17A-17B, in various embodiments, the needle may be formed from a metal tube 1600, including, but not limited to, stainless steel, and the tip 1610 may be formed using a die 1608. In the exemplary embodiment that follows, the tube 1600 is heated to the desired temperature for molding using Radio Frequency ("RF") energy. In the exemplary embodiment, as described below, use of RF energy at a frequency of 2.45 GHz is described. However, in various other embodiments, other RF frequencies may be used, including, but not limited to, 27.10 MHz. In the various embodiments, the source of the RF energy may vary. Additionally, where the RF frequency varies, the resonant tank circuit will vary accordingly.

Figure 17A:
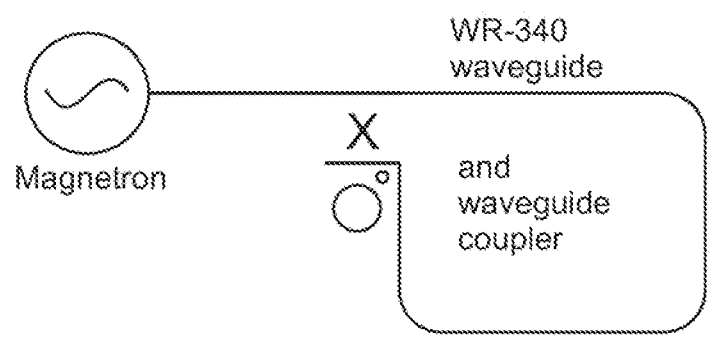
FIGS. 17A and 17B are illustrations of a magnetron and a circuit according to one embodiment of the method.
Figure 17B:
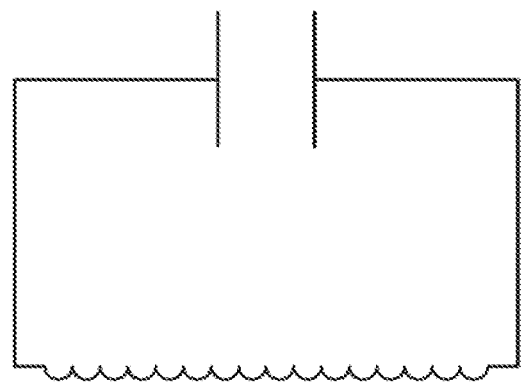

In some embodiments, the RF energy may be produced by a magnetron, producing RF waves at a frequency of 2.45 GHz. In the exemplary embodiment, the die cavity 1608 is formed in a metal block 1602, which may be any type of steel or another metal appropriately used as a die to form the needle tip. A spring-like assembly 1604, which may be made from beryllium copper, or any other metal, is included and maintains contact with the tube 1600 as the tube approaches the die cavity 1608. Although described herein in the exemplary embodiment as being "spring-like", other methods may be used to maintain the contact of the assembly 1604 with the tube 1600. The die block 1602, spring-like assembly 1604 and the tube 1600 together create the inductor of the circuit as illustrated in FIG. 17B. The air gap distance 1606 is the capacitor of the circuit as illustrated in FIG. 17B, and is formed between the tube 1600 and the die cavity 1608.

To achieve a resonance of 2.45 GHz in the circuit (i.e., a resonant tank circuit), the appropriate capacitance must be achieved against the inductance. As the inductance is fixed, the capacitance is a function of the distance 1606 between the tube 1600 and the die cavity 1608. The distance may be different for different realizations of the mechanical configuration.

In the exemplary embodiment, a magnetron may be used to provide energy at 2.45 GHz into a waveguide. The assembly as described above is in communication with the waveguide such that the assembly is heated by the 2.45 GHz energy (see FIG. 17A).

Figure 16A:
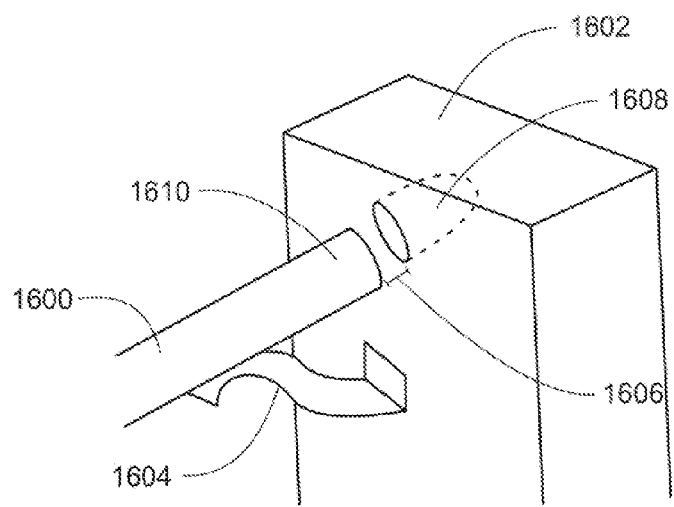
FIGS. 16A-16C are illustrative views of a method of making a needle according to one embodiment.
Figure 16B:
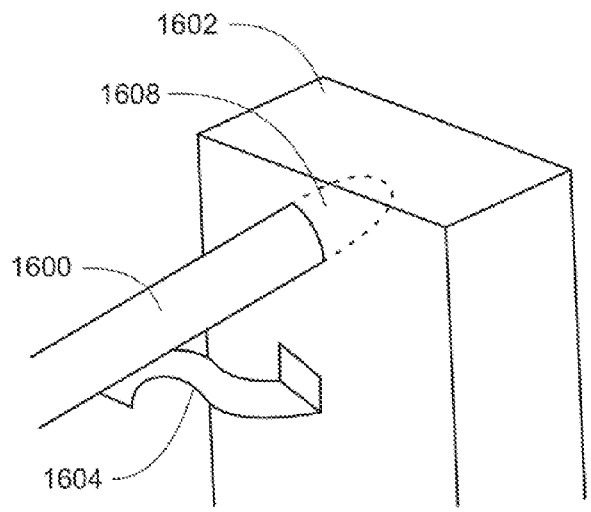
Figure 16C:
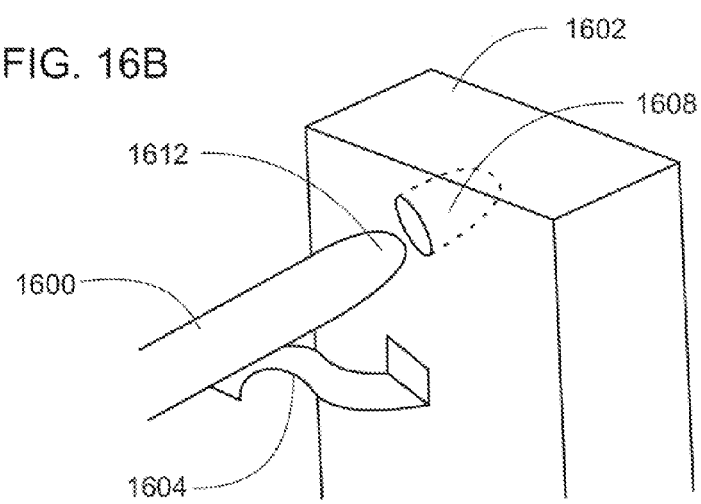

As shown in FIG. 16A, as the tube 1600 approaches the die cavity 1608, the tube 1600 contacts the spring-like assembly 1604 and the distance 1606 decreases. At a distance 1606, the resonant tank circuit is achieved. As the distance 1606 reaches the necessary capacitance, the plasma arc is formed. After the tip 1610 is exposed to the plasma arc for an appropriate amount of time, the plasma arc melts the tip 1610 of the tube 1600. At the proper time, e.g., when the metal is at the appropriate temperature to enter the die cavity 1608, the tip 1610 enters the die cavity 1608, as shown in FIG. 16B. The tip 1610 remains in the die cavity 1608 for an appropriate time to form the desired tip shape. After the appropriate time passes, the tube 1600 is removed from the die cavity 1608, and as illustrated in FIG. 16C, the tip 1612 has been formed by the die cavity 1608. The tube 1600 may then be removed from communication with the waveguide.

The methods described above may be implemented in various embodiments for manufacture including but not limited to, high volume manufacture, where any number of needles, for example, but not limited to, 1-100,000, for example, needles are manufactured simultaneously. With respect to the embodiments described herein, therefore, although the description discusses a singular tube, die cavity, etc., this is not intended to be limited, rather, be an illustration of one embodiment. Multiples of one or more of the elements discussed may be used in the manufacture of 1 or more needles.

In some embodiments, for example, the die cavity 1608 may be flush with the inside of the waveguide which is in direct communication with the magnetron. An automated control system, controlled by a feedback loop, may be used to advance the tubes into the waveguide and towards the spring-like assembly 1604 and the die cavity 1608. In addition, one or more light sensors/optical sensors may be used to detect the plasma arc formation. The one or more light sensors may send a signal to a motion control system to advance the tubes 1600. In addition, one or more temperature sensors may be used to determine the appropriate time to advance the tube 1600 into the die cavity 1608 and/or to remove the tube 1600 from the die cavity 1608. Additional sensors may be used to detect motion, temperature, light and/or 2.45 GHz energy. Also, in some embodiments, one or more timers may be used in the feedback loop. Although a magnetron is described with respect to the exemplary embodiments, in some embodiments, another source of 2.45 GHz energy may be used.

Figure 18A:
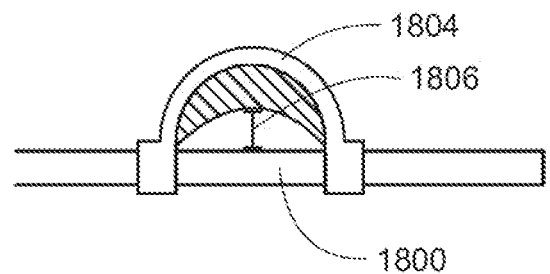
FIG. 18A is an illustration of one method according to one embodiment.
Figure 18B:
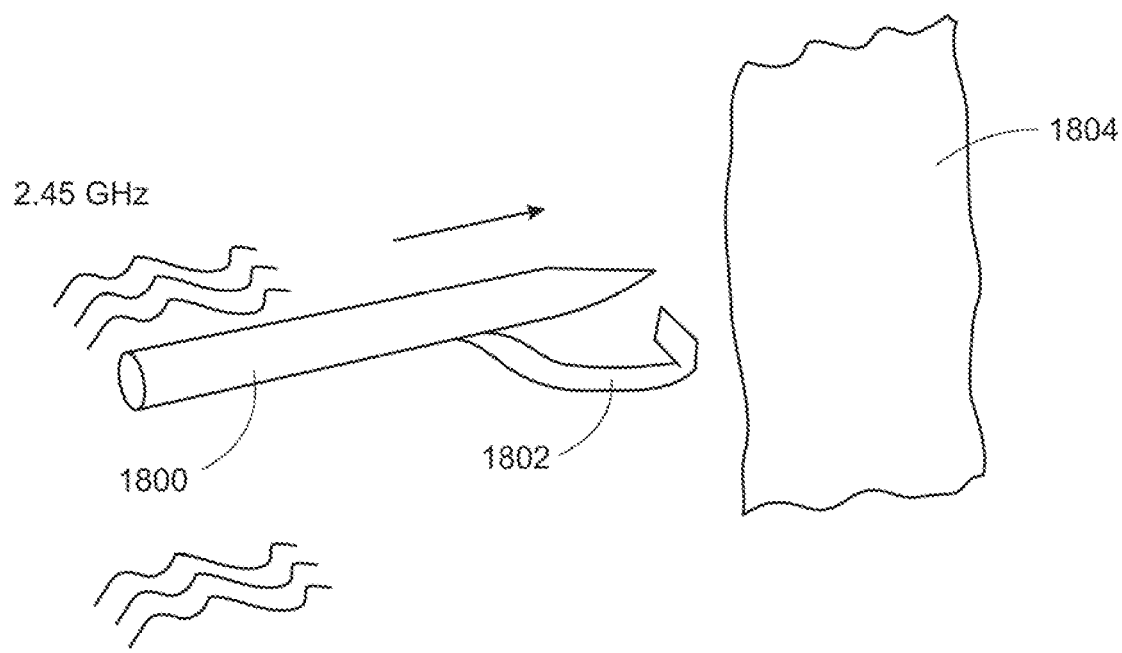
FIG. 18B is an illustration of one method according to one embodiment.

Referring now to FIGS. 18A-18B, in other embodiments, a tube or needle 1800, made from stainless steel or any other metal, may be connected, either removably or crimped together, to a metal part 1804, for example, a copper part, to form the inductor. In some embodiments, the metal part 1804 may be crimped to the needle (see FIG. 18A). The distance 1806 or gap between needle 1800 and the metal part 1804, together with the application of RF at 2.45 GHz, completes a resonant tank circuit and a plasma arc may be formed. This will heat the needle 1800. As described above, one or more sensors, for example, but not limited to, optical and/or temperature, may be used to provide feedback to a control loop and/or processor, to control the duration of the heating of the metal needle 1800.

Referring now to FIG. 18B, the methods described above may be used in various processes and method of manufacture, where controlled heating of a metal or other material surface is desired. For example, a the metal part 1.802 could take on any form, and as an example, could be a spring-like assembly as discussed above with respect to FIGS. 16A-16C. The needle 1800 may approach the metal part 1802, completing the resonant tank circuit. Once a plasma arc is formed, at an appropriate time, for example, as the plasma arc diminishes (again, one or more sensors and/or timers, as discussed above, may be used to determine when the plasma arc forms and diminishes) the needle 1800 may advance towards a contact, which mayh be a plastic part 1804, which may be any object or contact made from plastic, including, but not limited to, a bag and/or tube, and the plastic may be any type of plastic, including, but not limited to, PVC, PTFE and/or polyurathane. In some embodiments, the contact may not be plastic. As the arc diminishes, while the needle 1800 is being pushed into the plastic part 1804, the plastic part 1804 may melt and then cool about the needle 1800. This process may produce a sterile connection between a plastic part 1804 and a needle 1800.

Figure 19A:
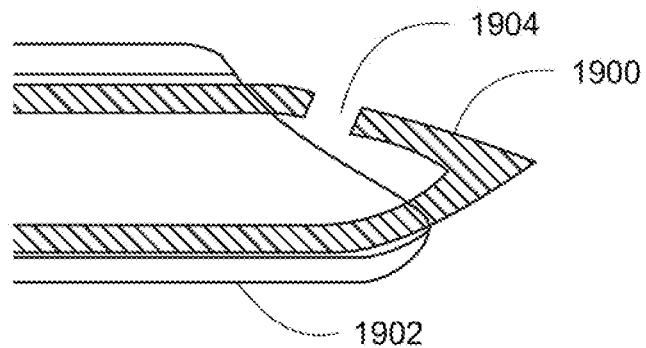
FIGS. 19A and 19B are illustrative examples of one method of making a needle according to one embodiment.
Figure 19B:
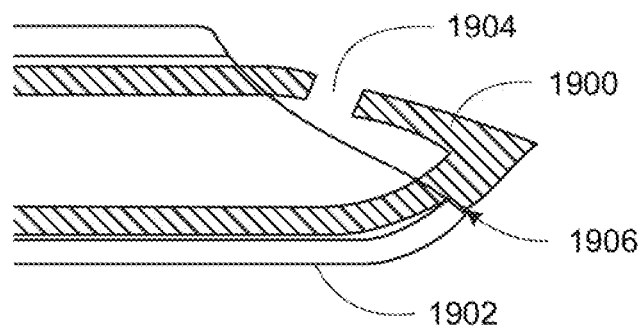

Referring now to FIGS. 19A and 19B, in some embodiments, the catheter and introduction needle assembly may include a relief feature in the needle to reduce the effect of the transition between the needle keep and the catheter tip. As shown in FIG. 19A, the needle 1900, having a needle hole or opening 1904 includes a catheter 1902 about the needle 1900. The catheter and needle assembly embodiment is described in more detail above. However, this may provide a discontinuous profile at the transition from the needle 1900 keel to the catheter 1902 tip. Referring now to FIG. 19B, in some embodiments, a relief feature 1906 may be introduced into the needle 1900. The relief feature 1900 may be introduced using one or more of, but not limited to, the following methods: machining, grinding, forging, indented, and/or etched. In some embodiments, the relief feature 1906 may smooth the transition from needle 1900 to catheter 1902 while not prohibiting the catheter 1902 to slide forward off of the introduction needle 1900 at insertion. Although one embodiment of the relief is shown and described herein, other shapes, sizes and embodiments are considered and may vary from that which is described herein.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed is:

1. An insertion device comprising:
    a base portion;
    a top portion slidably connected to the base portion;
    an introduction needle;
    a catheter in slidable relation to the introduction needle;
    a substantially cylindrical flash chamber, the flash chamber having an inlet in fluid communication with the introduction needle;
    wherein the flash chamber is connected to the base portion, and
    wherein the top portion slidably engages with the flash chamber, and
    wherein when the top portion slidably advances towards the introduction needle the top portion maintains slidable engagement with the flash chamber while advancing;
    a locking mechanism having a first end and a second end, the locking mechanism located on the base portion; and
    a clip connected to the top portion, wherein the clip adapted to accommodate and control the locking mechanism and wherein the clip slidably engages the locking mechanism,
    wherein as the top portion slidably advances with respect to the base portion, the clip slidably advances from the first end of the locking mechanism to the second end of the mechanism, whereby the locking mechanism moves from an unlocked to a locked position and whereby in the locked position, the top portion is positioned about the needle.

2. The insertion device of claim 1, wherein the flash chamber further comprising an insert.

3. The insertion device of claim 2, wherein the insert is a cylindrical insert.

4. The insertion device of claim 2, wherein the insert comprising a color contrasting to the color of a flash fluid.

5. The insertion device of claim 2, wherein the insert comprising a wicking material.

6. The insertion device of claim 5, wherein the wicking material further comprising an assay test strip wherein the assay test strip indicates the presence of one or more indicators in a fluid.

7. The insertion device of claim 1, wherein the flash chamber further comprising a filter.

8. The insertion device of claim 7 wherein the filter comprising a membrane material.

9. The insertion device of claim 1, wherein the flash chamber further comprising an expandable membrane in fluid communication with the introduction needle.

10. The insertion device of claim 1 further comprising a needle guard removably connected to the base portion.

11. The insertion device of claim 1 wherein the top portion further comprising an opening to at least a portion of the flash chamber whereby the flash chamber may be viewed.

12. The insertion device of claim 1, further comprising:
    a locking mechanism, wherein as the top portion advances with respect to the base portion, the locking mechanism moves from an unlocked position to a locked position, whereby in the locked position, the top portion is positioned about the needle.

13. The insertion device of claim 1, wherein the catheter further comprising:
    a distal end comprising a non-perpendicular angle to the axis of the catheter and conforming to a keel of the introduction needle.

14. An insertion device comprising:

a base portion;

a top portion slidably connected to the base portion;

a substantially cylindrical flash chamber, the flash chamber having an inlet and adapted for connection to an introduction needle, wherein the top portion slidably engages with the flash chamber; and a locking mechanism having a first end and a second end, the locking mechanism located on the base portion; and a clip connected to the top portion, wherein the clip adapted to accommodate and control the locking mechanism and wherein the clip slidably engages the locking mechanism, wherein as the top portion slidably advances with respect to the base portion, the clip slidably advances from the first end of the locking mechanism to the second end of the mechanism, whereby the locking mechanism moves from an unlocked to a locked position and whereby in the locked position, the top portion is positioned about the introduction needle.

15. The insertion device of claim 14, wherein the flash chamber further comprising an insert.

16. The insertion device of claim 14, wherein the insert is a cylindrical insert.

* * * * *